(12) United States Patent
Taylor et al.

(10) Patent No.: US 11,648,411 B2
(45) Date of Patent: *May 16, 2023

(54) DEFIBRILLATION WAVEFORMS FOR A WEARABLE CARDIAC DEFIBRILLATOR

(71) Applicant: West Affum Holdings DAC, Dublin (IE)

(72) Inventors: Tyson G. Taylor, Bothell, WA (US); Douglas K. Medema, Everett, WA (US)

(73) Assignee: West Affum Holdings DAC, Dublin (IE)

( * ) Notice: Subject to any disclaimer, the term of this patent is extended or adjusted under 35 U.S.C. 154(b) by 204 days.

This patent is subject to a terminal disclaimer.

(21) Appl. No.: 17/201,575

(22) Filed: Mar. 15, 2021

(65) Prior Publication Data

US 2021/0196965 A1 Jul. 1, 2021

Related U.S. Application Data

(63) Continuation of application No. 15/794,585, filed on Oct. 26, 2017, now Pat. No. 10,946,207.

(Continued)

(51) Int. Cl.
*A61N 1/39* (2006.01)
*A61N 1/04* (2006.01)

(52) U.S. Cl.
CPC ......... *A61N 1/3937* (2013.01); *A61N 1/3904* (2017.08); *A61N 1/046* (2013.01); *A61N 1/3906* (2013.01); *A61N 1/3987* (2013.01)

(58) Field of Classification Search
CPC .. A61N 1/3904; A61N 1/3906; A61N 1/3937; A61N 1/3943
See application file for complete search history.

(56) References Cited

U.S. PATENT DOCUMENTS

| 3,724,455 A | 4/1973 | Unger |
|---|---|---|
| 4,583,524 A | 4/1986 | Hutchins |

(Continued)

FOREIGN PATENT DOCUMENTS

| EP | 0281219 A1 | 9/1988 |
|---|---|---|
| EP | 0420563 A2 | 4/1991 |

(Continued)

OTHER PUBLICATIONS

Fennigkoh, A Comparison of Defibrillator Waveform Characteristics—An Evaluation for Aurora Healthcare, ResearchGate, Jun. 2019, DOI:10.13140/RG 2.1.3480.5205, Milwaukee School of Engineering, Milwaukee, WI, USA.

(Continued)

*Primary Examiner* — Alyssa M Alter
(74) *Attorney, Agent, or Firm* — Spectrum IP Law Group LLC

(57) ABSTRACT

An external defibrillator system is configured with at least two different algorithms for determining the duration of a shock administered to a patient being treated and selects the algorithm based on one or more patient parameters such as, for example, the patient's TTI. The patient's TTI can be measured prior to or while the shock is being administered to the patient. The shock can be, for example, a multiphasic defibrillation or a multiphasic cardioversion shock. The charge voltage of the system's energy storage device can additionally be varied depending on the one or more patient parameters. For example, the system may charge the energy storage device so that the charge voltage is higher or lower than a nominal charge voltage responsive to the patient's TTI is higher or lower compared to an average TTI, respectively.

20 Claims, 9 Drawing Sheets

Related U.S. Application Data

(60) Provisional application No. 62/550,518, filed on Aug. 25, 2017, provisional application No. 62/512,003, filed on May 27, 2017.

(56) References Cited

U.S. PATENT DOCUMENTS

| | | |
|---|---|---|
| 4,619,265 A | 10/1986 | Morgan et al. |
| 4,800,883 A | 1/1989 | Winstrom |
| 4,821,723 A | 4/1989 | Baker, Jr. et al. |
| 4,928,690 A | 5/1990 | Heilman et al. |
| 4,953,551 A | 9/1990 | Mehra et al. |
| 4,955,381 A | 9/1990 | Way et al. |
| 5,078,134 A | 1/1992 | Heilman et al. |
| 5,161,528 A | 11/1992 | Sweeney |
| 5,228,449 A | 7/1993 | Christ et al. |
| 5,237,989 A | 8/1993 | Morgan et al. |
| 5,344,429 A | 9/1994 | Smits |
| 5,346,506 A | 9/1994 | Mower et al. |
| 5,348,008 A | 9/1994 | Bomn et al. |
| 5,352,239 A | 10/1994 | Pless |
| 5,353,793 A | 10/1994 | Bomn |
| RE34,800 E | 11/1994 | Hutchins |
| 5,366,485 A | 11/1994 | Kroll et al. |
| 5,369,351 A | 11/1994 | Adams |
| 5,372,606 A | 12/1994 | Lang et al. |
| 5,376,105 A | 12/1994 | Hedberg |
| 5,394,892 A | 3/1995 | Kenny et al. |
| 5,405,362 A | 4/1995 | Kramer et al. |
| 5,425,748 A | 6/1995 | Pless |
| 5,433,729 A | 7/1995 | Adams et al. |
| 5,468,254 A | 11/1995 | Hahn et al. |
| 5,474,574 A | 12/1995 | Payne et al. |
| 5,507,779 A | 4/1996 | Altman |
| 5,531,765 A | 7/1996 | Pless |
| 5,531,770 A | 7/1996 | Kroll et al. |
| 5,540,721 A | 7/1996 | Kroll |
| 5,578,062 A | 11/1996 | Alt et al. |
| 5,607,385 A | 3/1997 | Francischelli et al. |
| 5,620,464 A | 4/1997 | Kroll et al. |
| 5,632,267 A | 5/1997 | Hognelid et al. |
| 5,634,938 A | 6/1997 | Swanson et al. |
| 5,645,573 A | 7/1997 | Kroll et al. |
| 5,662,690 A | 9/1997 | Cole et al. |
| 5,674,266 A | 10/1997 | Stendahl |
| 5,713,924 A | 2/1998 | Min et al. |
| 5,718,718 A | 2/1998 | Kroll et al. |
| 5,722,995 A | 3/1998 | Olson et al. |
| 5,725,560 A | 3/1998 | Brink |
| 5,735,879 A | 4/1998 | Gliner et al. |
| 5,782,878 A | 7/1998 | Morgan et al. |
| 5,792,189 A | 8/1998 | Gray et al. |
| 5,792,204 A | 8/1998 | Snell |
| 5,797,967 A | 8/1998 | Kenknight |
| 5,803,927 A | 9/1998 | Cameron et al. |
| 5,873,893 A | 2/1999 | Sullivan et al. |
| 5,891,172 A | 4/1999 | Stendahl et al. |
| 5,899,924 A | 5/1999 | Brewer et al. |
| 5,902,249 A | 5/1999 | Lyster |
| 5,902,323 A | 5/1999 | Brewer et al. |
| 5,908,442 A | 6/1999 | Brewer et al. |
| 5,913,685 A | 6/1999 | Hutchins |
| 5,928,270 A | 7/1999 | Ramsey |
| 5,944,669 A | 8/1999 | Kaib |
| 5,968,080 A | 10/1999 | Brewer et al. |
| 5,974,339 A | 10/1999 | Baker, Jr. et al. |
| 5,978,706 A | 11/1999 | Brewer et al. |
| 5,999,852 A | 12/1999 | Elabbady et al. |
| 6,035,235 A | 3/2000 | Perttu et al. |
| 6,041,254 A | 3/2000 | Sullivan et al. |
| 6,047,203 A | 4/2000 | Sackner et al. |
| 6,047,211 A | 4/2000 | Swanson et al. |
| 6,065,154 A | 5/2000 | Hulings et al. |
| 6,108,197 A | 8/2000 | Janik |
| 6,148,233 A | 11/2000 | Owen et al. |
| 6,173,204 B1 | 1/2001 | Sullivan et al. |
| 6,181,967 B1 | 1/2001 | Alt |
| 6,201,992 B1 | 3/2001 | Freeman |
| 6,208,896 B1 | 3/2001 | Mulhauser |
| 6,230,054 B1 | 5/2001 | Powers |
| 6,253,105 B1 | 6/2001 | Leyde |
| 6,263,238 B1 | 7/2001 | Brewer et al. |
| 6,263,239 B1 | 7/2001 | Brewer et al. |
| 6,287,328 B1 | 9/2001 | Snyder et al. |
| 6,292,691 B1 | 9/2001 | Pendekanti et al. |
| 6,304,780 B1 | 10/2001 | Owen et al. |
| 6,319,011 B1 | 11/2001 | Motti et al. |
| 6,334,070 B1 | 12/2001 | Nova et al. |
| 6,356,785 B1 | 3/2002 | Snyder et al. |
| 6,370,428 B1 | 4/2002 | Snyder et al. |
| 6,408,206 B1 | 6/2002 | Kroll et al. |
| 6,415,179 B1 | 7/2002 | Pendekanti et al. |
| 6,421,563 B1 | 7/2002 | Sullivan et al. |
| 6,427,083 B1 | 7/2002 | Owen et al. |
| 6,437,083 B1 | 8/2002 | Brack et al. |
| 6,438,419 B1 | 8/2002 | Callaway et al. |
| 6,456,877 B1 | 9/2002 | Fishler |
| 6,477,413 B1 | 11/2002 | Sullivan et al. |
| 6,480,738 B2 | 11/2002 | Irnich |
| 6,487,448 B2 | 11/2002 | Sullivan et al. |
| 6,529,875 B1 | 3/2003 | Nakajima et al. |
| 6,539,255 B1 | 3/2003 | Brewer et al. |
| 6,539,258 B1 | 3/2003 | Sullivan et al. |
| 6,546,285 B1 | 4/2003 | Owen et al. |
| 6,546,287 B1 | 4/2003 | Havel et al. |
| 6,567,698 B2 | 5/2003 | Herleikson |
| 6,597,949 B1 | 7/2003 | Dhurjaty |
| 6,633,778 B2 | 10/2003 | Sherman |
| 6,647,290 B2 | 11/2003 | Wuthrich |
| 6,671,545 B2 | 12/2003 | Fincke |
| 6,671,546 B2 | 12/2003 | Cansell et al. |
| 6,681,003 B2 | 1/2004 | Linder et al. |
| 6,738,664 B1 | 5/2004 | McDaniel |
| 6,760,621 B2 | 7/2004 | Walcott et al. |
| 6,762,917 B1 | 7/2004 | Verbiest et al. |
| 6,778,860 B2 | 8/2004 | Ostroff et al. |
| 6,813,517 B2 | 11/2004 | Daynes et al. |
| 6,834,204 B2 | 12/2004 | Ostroff et al. |
| 6,839,590 B2 | 1/2005 | Waltman |
| 6,904,314 B1 | 6/2005 | Brewer et al. |
| 6,952,607 B2 | 10/2005 | Mulhauser |
| 6,963,773 B2 | 11/2005 | Waltman et al. |
| 6,968,230 B2 | 11/2005 | Waltman |
| 6,980,856 B2 | 12/2005 | Sullivan et al. |
| 6,996,436 B2 | 2/2006 | Allen et al. |
| 7,006,865 B1 | 2/2006 | Cohen et al. |
| 7,062,321 B2 | 6/2006 | Lyster et al. |
| 7,065,401 B2 | 6/2006 | Worden |
| 7,072,712 B2 | 7/2006 | Kroll et al. |
| 7,079,894 B2 | 7/2006 | Lyster et al. |
| 7,136,702 B2 | 11/2006 | Wanasek |
| 7,142,927 B2 | 11/2006 | Benser et al. |
| 7,174,208 B2 | 2/2007 | Degroot et al. |
| 7,203,539 B2 | 4/2007 | Ware et al. |
| 7,308,305 B1 | 12/2007 | Province et al. |
| 7,328,065 B2 | 2/2008 | Watanabe et al. |
| 7,340,301 B2 | 3/2008 | Weiss et al. |
| 7,389,139 B2 | 6/2008 | Ostroff |
| 7,463,923 B2 | 12/2008 | Brewer et al. |
| 7,522,958 B2 | 4/2009 | Ideker et al. |
| 7,559,902 B2 | 7/2009 | Ting et al. |
| 7,865,238 B2 | 1/2011 | Brink |
| 7,870,761 B2 | 1/2011 | Valentine et al. |
| 7,962,207 B2 | 6/2011 | Nassif |
| 7,974,689 B2 | 7/2011 | Volpe et al. |
| 8,032,213 B1 | 10/2011 | Qu et al. |
| 8,036,742 B2 | 10/2011 | Sullivan et al. |
| 8,090,437 B2 | 1/2012 | Sullivan et al. |
| 8,135,462 B2 | 3/2012 | Owen et al. |
| 8,140,154 B2 | 3/2012 | Donnelly et al. |
| 8,145,300 B2 | 3/2012 | Powers |
| 8,145,303 B2 | 3/2012 | Rubin et al. |
| 8,150,511 B2 | 4/2012 | Pittaro |
| 8,364,260 B2 | 1/2013 | Kumar |

(56) References Cited

U.S. PATENT DOCUMENTS

| | | |
|---|---|---|
| 8,369,944 B2 | 2/2013 | Macho et al. |
| 8,396,566 B2 | 3/2013 | Kassab et al. |
| 8,401,638 B2 | 3/2013 | Swerdlow et al. |
| 8,423,137 B2 | 4/2013 | Moulder |
| 8,489,187 B2 | 7/2013 | Linder et al. |
| 8,548,557 B2 | 10/2013 | Garstka et al. |
| 8,615,295 B2 | 12/2013 | Savage et al. |
| 8,644,925 B2 | 2/2014 | Volpe et al. |
| 8,838,233 B2 | 9/2014 | Kelly et al. |
| 8,897,860 B2 | 11/2014 | Volpe et al. |
| 8,904,214 B2 | 12/2014 | Volpe et al. |
| 8,965,500 B2 | 2/2015 | Macho et al. |
| 8,965,501 B2 | 2/2015 | Sullivan |
| 9,008,801 B2 | 4/2015 | Kaib et al. |
| 9,056,207 B2 | 6/2015 | Shao et al. |
| 9,089,685 B2 | 7/2015 | Sullivan et al. |
| 9,131,901 B2 | 9/2015 | Volpe et al. |
| 9,132,267 B2 | 9/2015 | Kaib |
| 9,174,061 B2 | 11/2015 | Freeman et al. |
| 9,308,383 B2 | 4/2016 | Didon |
| 9,370,665 B2 | 6/2016 | Hampton et al. |
| 9,408,548 B2 | 8/2016 | Volpe et al. |
| 9,415,230 B2 | 8/2016 | Powers |
| 9,454,219 B2 | 9/2016 | Volpe et al. |
| 9,480,852 B2 | 11/2016 | Bonnamy |
| 9,522,284 B2 | 12/2016 | Ostroff |
| 9,592,403 B2 | 3/2017 | Sullivan |
| 9,604,070 B2 | 3/2017 | Sullivan et al. |
| 9,616,243 B2 | 4/2017 | Raymond et al. |
| 9,616,244 B2 | 4/2017 | Anderson et al. |
| 9,623,258 B2 | 4/2017 | Trayanova et al. |
| 9,717,924 B2 | 8/2017 | Snyder |
| 9,757,577 B2 | 9/2017 | Ideker et al. |
| 9,789,326 B2 | 10/2017 | Schwibner et al. |
| 10,946,207 B2 * | 3/2021 | Taylor .................. A61N 1/3904 |
| 2011/0022105 A9 | 1/2003 | Owen et al. |
| 2003/0125771 A1 | 7/2003 | Garrett |
| 2003/0153951 A1 | 8/2003 | Ideker et al. |
| 2003/0158593 A1 | 8/2003 | Heilman et al. |
| 2003/0167075 A1 | 9/2003 | Fincke |
| 2003/0216786 A1 | 11/2003 | Russial |
| 2003/0229379 A1 | 12/2003 | Ramsey |
| 2004/0044371 A1 | 3/2004 | Tamura et al. |
| 2004/0088011 A1 | 5/2004 | Snyder et al. |
| 2004/0138713 A1 | 7/2004 | Stickney et al. |
| 2004/0143297 A1 | 7/2004 | Ramsey |
| 2005/0090868 A1 | 4/2005 | Cansell |
| 2005/0107833 A1 | 5/2005 | Freeman et al. |
| 2005/0107834 A1 | 5/2005 | Freeman et al. |
| 2006/0097923 A1 | 5/2006 | Li et al. |
| 2006/0111750 A1 | 5/2006 | Bowers |
| 2006/0229679 A1 | 10/2006 | Joo |
| 2007/0100381 A1 | 5/2007 | Snyder et al. |
| 2008/0086175 A1 | 4/2008 | Libbus et al. |
| 2008/0195161 A1 | 8/2008 | Sakuma et al. |
| 2008/0312709 A1 | 12/2008 | Volpe et al. |
| 2009/0005827 A1 | 1/2009 | Weintraub et al. |
| 2009/0306730 A1 | 12/2009 | Roso |
| 2010/0007413 A1 | 1/2010 | Herleikson et al. |
| 2010/0063559 A1 | 3/2010 | McIntyre et al. |
| 2010/0298899 A1 | 11/2010 | Donnelly et al. |
| 2011/0106190 A1 | 5/2011 | Foeller et al. |
| 2011/0288604 A1 | 11/2011 | Kaib et al. |
| 2011/0288605 A1 | 11/2011 | Kaib et al. |
| 2012/0150008 A1 | 1/2012 | Lanar et al. |
| 2012/0035677 A1 | 2/2012 | Imabayashi et al. |
| 2012/0112903 A1 | 5/2012 | Kaib et al. |
| 2012/0123492 A1 | 5/2012 | Hunt et al. |
| 2012/0144551 A1 | 6/2012 | Guldalian |
| 2012/0158075 A1 | 6/2012 | Kaib et al. |
| 2012/0265265 A1 | 10/2012 | Razavi et al. |
| 2012/0283794 A1 | 11/2012 | Kaib et al. |
| 2012/0293323 A1 | 11/2012 | Kaib et al. |
| 2012/0302860 A1 | 11/2012 | Volpe et al. |
| 2012/0310315 A1 | 12/2012 | Savage et al. |
| 2013/0085538 A1 | 4/2013 | Volpe et al. |
| 2013/0190833 A1 | 7/2013 | Azar et al. |
| 2013/0231711 A1 | 9/2013 | Kaib |
| 2013/0245388 A1 | 9/2013 | Rafferty et al. |
| 2013/0274565 A1 | 10/2013 | Langer et al. |
| 2013/0317852 A1 | 11/2013 | Worrell et al. |
| 2013/0325078 A1 | 12/2013 | Whiting et al. |
| 2014/0025131 A1 | 1/2014 | Sullivan et al. |
| 2014/0070957 A1 | 3/2014 | Longinotti-Buitoni et al. |
| 2014/0107718 A1 | 4/2014 | Foote et al. |
| 2014/0163663 A1 | 6/2014 | Poddar et al. |
| 2014/0324112 A1 | 10/2014 | Macho et al. |
| 2014/0371806 A1 | 12/2014 | Raymond et al. |
| 2014/0378812 A1 | 12/2014 | Saroka et al. |
| 2015/0039053 A1 | 2/2015 | Kaib et al. |
| 2015/0328472 A1 | 11/2015 | Sullivan et al. |
| 2016/0004831 A1 | 1/2016 | Carlson et al. |
| 2016/0082277 A1 | 3/2016 | Foshee, Jr. et al. |
| 2016/0136447 A1 | 5/2016 | Herleikson |
| 2016/0271408 A1 | 9/2016 | Newton et al. |
| 2017/0252571 A1 | 9/2017 | Dascoli et al. |

FOREIGN PATENT DOCUMENTS

| | | |
|---|---|---|
| EP | 0473002 A3 | 5/1992 |
| EP | 0641573 A3 | 6/1997 |
| EP | 0574609 B1 | 12/1998 |
| EP | 0540266 B1 | 12/1999 |
| EP | 0589251 B1 | 11/2000 |
| EP | 1259291 A1 | 11/2002 |
| EP | 1259290 B1 | 4/2004 |
| EP | 1429840 A1 | 6/2004 |
| EP | 0966312 B1 | 8/2004 |
| EP | 1461121 A1 | 9/2004 |
| EP | 1023920 B1 | 11/2006 |
| EP | 2229978 A1 | 9/2010 |
| EP | 2446927 A1 | 5/2012 |
| EP | 2424617 B1 | 7/2013 |
| EP | 1284788 B1 | 8/2014 |
| EP | 1458445 B1 | 11/2015 |
| JP | 2010194318 A | 9/2010 |
| JP | 2012034843 A | 2/2012 |
| WO | 9738753 A1 | 10/1997 |
| WO | 9839061 A2 | 9/1998 |
| WO | 9903534 A1 | 1/1999 |
| WO | 9926695 A1 | 6/1999 |
| WO | 0121255 A1 | 3/2001 |
| WO | 0126731 A1 | 4/2001 |
| WO | 03039650 A2 | 5/2003 |
| WO | 2006067158 A1 | 6/2006 |
| WO | 2008020369 A1 | 2/2008 |
| WO | 2008068029 A1 | 6/2008 |
| WO | 2010067373 A3 | 8/2010 |
| WO | 2012147061 A2 | 11/2012 |
| WO | 2013049903 A1 | 4/2013 |
| WO | 2014201389 A1 | 12/2014 |
| WO | 2016141096 A1 | 9/2016 |
| WO | 2017037735 A1 | 3/2017 |

OTHER PUBLICATIONS

Gliner, Transthoracic Defibrillation of Swine with Monophasic and Biphasic Waveforms, Circulation, Sep. 15, 1995, pp. 1634-1643, vol. 92, Issue 6, American Heart Association, Dallas, TX, USA.

Sullivan, Heart-cell Model Response to Biphasic External Defibrillator Waveforms, Annals of Biomedical Engineering, Oct. 12-14, 2000, 28, p. S-52, (Suppl 1):S-52, Seattle, WA, USA.

Walcott, Choosing the Optimal Monophasic and Biphasic Waveforms for Ventricular Defibrillation, Journal of Cardiovascular Electrophysiology, Sep. 1995, vol. 6, No. 9, Wiley-Blackwell, Hoboken, NJ, USA.

Walker, Comparison of Clinically Used Biphasic Waveforms for External Defibrillation, Academic Emergency Medicine, May 2001, pp. 432-433, vol. 8, No. 5, Society for Academic Emergency Medicine, Des Plaines, IL, USA.

(56) References Cited

OTHER PUBLICATIONS

White, Predicting the Relative Efficacy of Shock Waveforms for Transthoracic Defibrillation in Dogs, Annals of Emergency Medicine, Sep. 1999, pp. 309-320, 34:3, American College of Emergency Physicians, Irving, TX, USA.

Heartstart MRx and XL AED Algorithm—Application Note, Jul. 2001, Edition 2 Philips Healthcare, USA.

Klein, H. U., Goldenberg I., & Moss, A. J., Risk Stratification for Implantable Cardioverter Defibrillator Therapy: The Role of the Wearable Cardioverter-Defibrillator, Clinical update, European Heart Journal, May 31, 2013, pp. 1-14, doi:10.1093/eurheartj/eht167, European Society of Cardiology.

Lifecor LifeVest System Model WCD 3100 Operator's Manual, 2006, PN 20B0040 Rev FI, Zoll Lifecor Corporation, Pittsburgh, PA.

LifeVest Model 4000 Patient Manual, Zoll, 2009, PN 20B0047 Rev B.

Pagan-Carlo, et al., "Encircling Overlapping Multipulse Shock Waveforms for Transthoracic Defibrillation," JACC Journals, Dec. 1998, vol. 32 Issue 7, p. 2065-2071.

The LifeVest Network/Patient Data Management System, Zoll, 2015, 2000503 Rev A.

\* cited by examiner

SAMPLE COMPONENTS OF WEARABLE CARDIOVERTER DEFIBRILLATOR (WCD) SYSTEM

SAMPLE COMPONENTS OF EXTERNAL DEFIBRILLATOR

DEFIBRILLATION WAVEFORMS FOR A WEARABLE CARDIAC DEFIBRILLATOR

CROSS REFERENCE TO RELATED PATENT APPLICATIONS

The present patent application is a continuation of U.S. application Ser. No. 15/794,585 filed Oct. 26, 2017, which in turn claims benefit of U.S. Application No. 62/512,003 filed May 27, 2017 and the benefit of U.S. Application No. 62/550,518 filed Aug. 25, 2017, all of which are hereby incorporated by reference in their entireties.

BACKGROUND

When people suffer from some types of heart arrhythmias, the result may be that blood flow to various parts of the body is reduced. Some arrhythmias may even result in a Sudden Cardiac Arrest (SCA). SCA can lead to death very quickly, e.g. within 10 minutes, unless treated in the interim.

Some people have an increased risk of SCA. People at a higher risk include patients who have had a heart attack, or a prior SCA episode. A frequent recommendation is for these people to receive an Implantable Cardioverter Defibrillator (ICD). The ICD is surgically implanted in the chest, and continuously monitors the patient's electrocardiogram (ECG). If certain types of heart arrhythmias are detected, then the ICD delivers an electric shock through the heart.

After being identified as having an increased risk of an SCA, and before receiving an ICD, these people are sometimes given a Wearable Cardioverter Defibrillator (WCD) system (early versions of such systems were called wearable cardiac defibrillator systems). A WCD system typically includes a harness, vest, or other garment that the patient is to wear. The WCD system further includes electronic components, such as a defibrillator and electrodes, coupled to the harness, vest, or other garment. When the patient wears the WCD system, the external electrodes may then make electrical contact with the patient's skin, and therefore can help determine the patient's ECG. If a shockable heart arrhythmia is detected, then the WCD system may deliver the appropriate electric shock through the patient's body to try to defibrillate or cardiovert the patient's heart.

SUMMARY

In embodiments, a system includes an external defibrillator configured with at least two different algorithms for determining the duration of a shock administered to a patient being treated. In some embodiments, the defibrillator is configured with at least three different algorithms for determining the duration of the shock. In some embodiments, the system can include a WCD.

In some embodiments, a method of delivering a shock is configured to select from at least two different algorithms for determining the duration of the shock. In some embodiments, the method selects from at least three different algorithms for determining the duration of the shock.

In some embodiments, the at least two algorithms for determining the duration can be based on the Walcott algorithm and the Constant Energy algorithm ("CE algorithm"). In some embodiments, the at least two duration algorithms include a third duration algorithm such as, for example, an algorithm that sets the duration to preconfigured maximum duration without regard to the patient's TTI or durations of the waveform's periods or phases (referred to herein as a "Max Duration algorithm"). In some embodiments, the maximum duration is less than or equal to 25 ms. In some embodiments, other shock duration algorithms can be used in place of or in addition to the Max Duration, Walcott and CE algorithms, including modified versions of the Max Duration, Walcott and CE algorithms.

In some embodiments, the shock can be, for example, a defibrillation shock or a cardioversion shock. In some embodiments, the shock can be a multiphasic shock such as, for example, a biphasic truncated exponential shock. In some embodiments, the system or method is configured to select the duration algorithm based on one or more patient parameters such as, for example, the patient's transthoracic impedance (TTI) or a time for an energy storage module to discharge to a selected or set ratio. In some embodiments, the one or more patient parameter is measured before the shock is administered, and in some other embodiments while the shock is being administered to the patient.

In some embodiments, an energy storage device such as, for example, a capacitor is used to provide the energy for the shock that is administered to the patient. In some embodiments, in addition to using two or more algorithms to determine the duration of the shock, the charge voltage of the energy storage device can be varied depending on the patient's TTI. For example, in some embodiments the system may charge the energy storage device so that the charge voltage is higher or lower than a nominal charge voltage responsive to the patient's TTI being higher or lower compared to a predetermined average TTI, respectively.

The foregoing brief summary is illustrative only and is not intended to be in any way limiting. In addition to the illustrative aspects, embodiments, and features described above, which need not all be present in all embodiments of the inventions disclosed herein, further aspects, embodiments, and features are set forth in the drawings and the following detailed description.

DETAILED DESCRIPTION

A wearable cardioverter defibrillator (WCD) system made according to embodiments has several components. These components can be provided separately as modules that can be interconnected, or can be combined with other components, etc.

Figure 1:
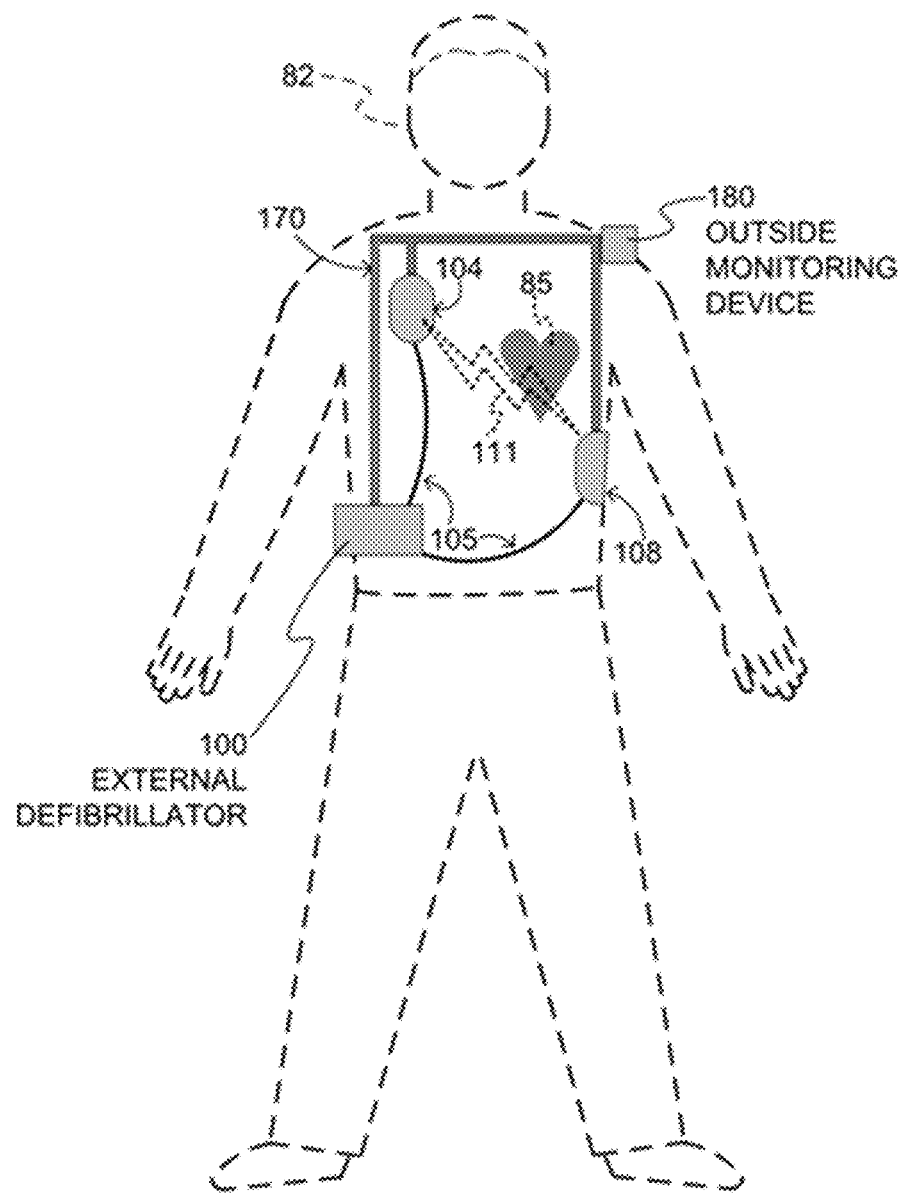
FIG. 1 is a diagram of components of a sample wearable cardioverter defibrillator (WCD) system, made according to embodiments.

FIG. 1 depicts a patient 82. Patient 82 may also be referred to as a person and/or wearer, since that patient wears components of the WCD system.

FIG. 1 also depicts components of a WCD system made according to embodiments. One such component is a support structure 170 that is wearable by patient 82. It will be understood that support structure 170 is shown generically in FIG. 1, and partly conceptually. FIG. 1 is provided to illustrate concepts about support structure 170, and is not to be construed as limiting how support structure 170 is implemented, or how it is worn.

Support structure 170 can be implemented in many different ways in different embodiments. For example, in one embodiment support structure 170 is be implemented in a single component or a combination of multiple components. In some embodiments, support structure 170 includes a vest, or a half-vest, or shirt, or other type garment, etc. In such embodiments, such items can be worn similarly to parallel articles of clothing. In some embodiments, support structure 170 include a harness, one or more belts or straps, etc. In such embodiments, such items can be worn by the patient around the torso, hips, over the shoulder, etc. In some embodiments, support structure 170 includes a container or housing, which in some embodiments is waterproof. In such embodiments, the support structure can be worn by being attached to the patient by adhesive material, for example as shown in U.S. Pat. No. 8,024,037. In some embodiments, support structure 170 is implemented as described for the support structure of US Pat. App. No. US 2017/0056682A1, which is incorporated herein by reference. Of course, in such embodiments, in view of this disclosure a person skilled in the art will recognize that additional components of the WCD system can be in the housing of a support structure instead of attached externally to the support structure, for example as described in the document incorporated by reference. There can be other examples.

A WCD system according to embodiments is configured to defibrillate a patient who is wearing it, by delivering an electrical charge to the patient's body in the form of an electric shock delivered in one or more pulses. FIG. 1 shows a sample external defibrillator 100, and sample defibrillation electrodes 104, 108, which are coupled to external defibrillator 100 via electrode leads 105. Defibrillator 100 and defibrillation electrodes 104, 108 are coupled to support structure 170. As such, many of the components of defibrillator 100 can be therefore coupled to support structure 170. When defibrillation electrodes 104, 108 make good electrical contact with the body of patient 82, defibrillator 100 can administer, via electrodes 104, 108, a brief, strong electric pulse 111 through the body. Pulse 111, also referred to herein as a shock, a defibrillation shock, a cardioversion shock, therapy or therapy shock, is intended to go through and restart heart 85, in an effort to save the life of patient 82. In some embodiments pulse 111 includes one or more pacing pulses, and so on.

A prior art defibrillator typically decides whether to defibrillate or not based on an ECG signal of the patient. However, external defibrillator 100 may initiate a shock (or hold-off a shock) based on a variety of inputs, with ECG merely being one of them.

Accordingly, in some embodiments of defibrillator 100, signals such as physiological signals containing physiological data are obtained from patient 82. While the patient may be a considered also a "user" of the WCD system, in some embodiments, for example, a user of the wearable cardioverter defibrillator (WCD) may be a clinician such as a doctor, nurse, emergency medical technician (EMT) or other similarly situated individual (or group of individuals). The particular context of these and other related terms within this description should be interpreted accordingly.

The WCD system may optionally include an outside monitoring device 180. Device 180 is called an "outside" device because it could be provided as a standalone device, for example not within the housing of defibrillator 100. Device 180 can be configured to sense or monitor at least one local parameter. A local parameter can be a parameter of patient 82, or a parameter of the WCD system, or a parameter of the environment, as will be described later in this document. Device 180 may include one or more transducers or sensors that are configured to render one or more physiological inputs from one or more patient parameters that it senses.

Optionally, device 180 is physically coupled to support structure 170. In addition, device 180 can be communicatively coupled with other components, which are coupled to support structure 170. Such communication can be implemented by a communication module, as will be deemed applicable by a person skilled in the art in view of this description.

Figure 2:
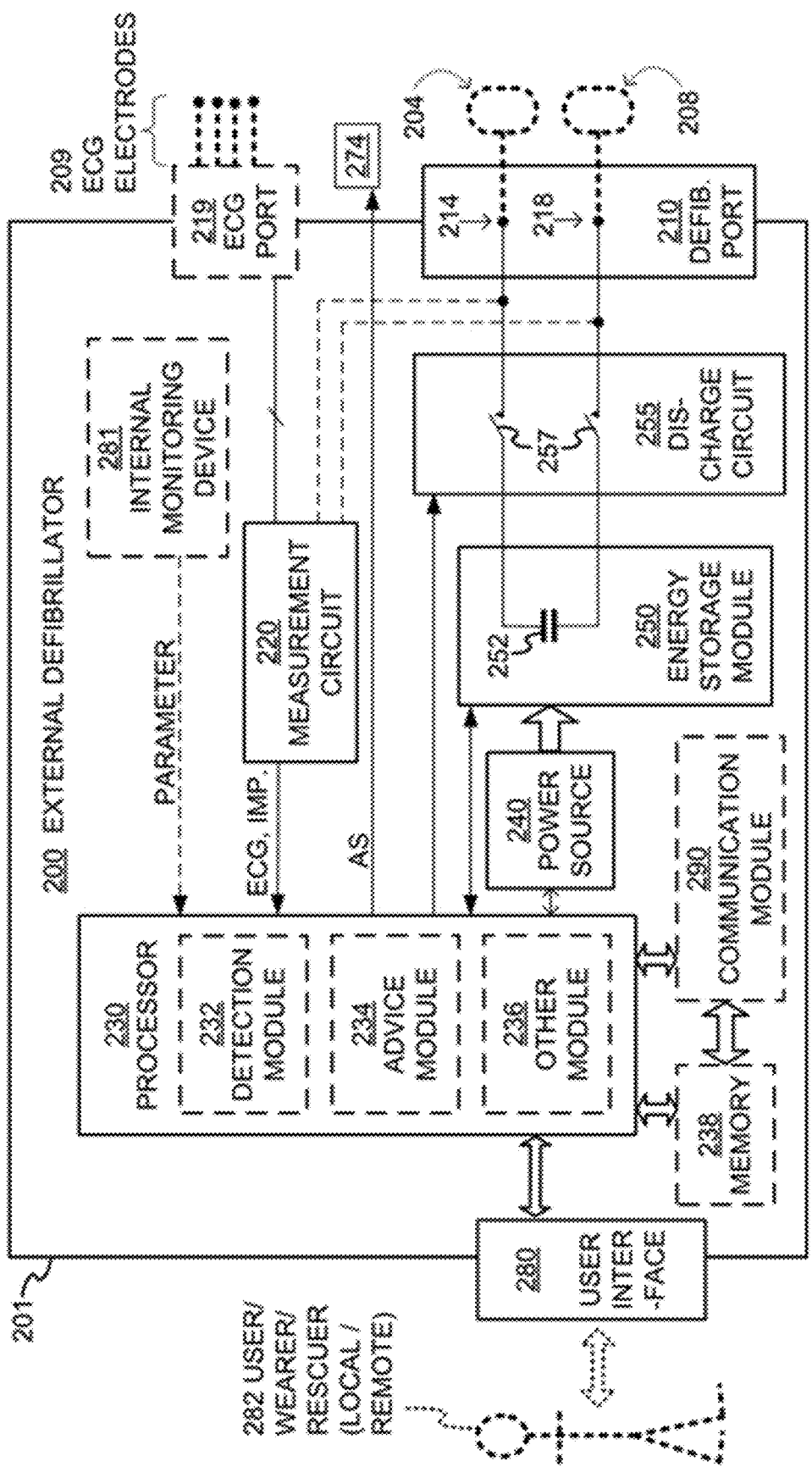
FIG. 2 is a diagram showing sample components of an external defibrillator, such as the one illustrated in the system of FIG. 1, and which is made according to embodiments.

FIG. 2 is a diagram showing components of an external defibrillator 200, made according to embodiments. These components can be, for example, included in external defibrillator 100 of FIG. 1. The components shown in FIG. 2 can be provided in a housing 201, which may also be referred to as casing 201.

External defibrillator 200 is intended for a patient who would be wearing it, such as patient 82 of FIG. 1. Defibrillator 200 may further include a user interface 280 for a user 282. User 282 can be patient 82, also known as wearer 82. Or user 282 can be a local rescuer at the scene, such as a bystander who might offer assistance, or a trained person. Or, user 282 might be a remotely located trained caregiver in communication with the WCD system.

User interface 280 can be made in many ways. User interface 280 may include output devices, which can be visual, audible or tactile, for communicating to a user by outputting images, sounds or vibrations. Images, sounds, vibrations, and anything that can be perceived by user 282 can also be called human perceptible indications. There are many examples of output devices. For example, an output device can be a light, or a screen to display what is sensed, detected and/or measured, and provide visual feedback to rescuer 282 for their resuscitation attempts, and so on. Another output device can be a speaker, which can be configured to issue voice prompts, beeps, loud alarm sounds to warn bystanders, etc.

User interface 280 may further include input devices for receiving inputs from users. Such input devices may additionally include various controls, such as pushbuttons, keyboards, touchscreens, one or more microphones, and so on. An input device can be a cancel switch, which is sometimes called an "I am alive" switch or "live man" switch. In some embodiments, actuating the cancel switch can prevent the impending delivery of a shock.

Defibrillator 200 may include an internal monitoring device 281. Device 281 is called an "internal" device because it is incorporated within housing 201. Monitoring device 281 can sense or monitor patient parameters such as patient physiological parameters, system parameters and/or environmental parameters, all of which can be called patient data. In other words, internal monitoring device 281 can be complementary or an alternative to outside monitoring device 180 of FIG. 1. Allocating which of the system parameters are to be monitored by which monitoring device can be done according to design considerations. Device 281 may include one or more transducers or sensors (not shown) that are configured to render one or more physiological inputs from one or more patient parameters that it senses.

Patient parameters may include patient physiological parameters. Patient physiological parameters may include, for example and without limitation, those physiological parameters that can be of any help in detecting by the wearable defibrillation system whether the patient is in need of a shock, plus optionally their medical history and/or event history. Examples of such parameters include the patient's ECG, blood oxygen level, blood flow, blood pressure, blood perfusion, pulsatile change in light transmission or reflection properties of perfused tissue, heart sounds, heart wall motion, breathing sounds and pulse. Accordingly, monitoring devices 180, 281 may include one or more sensors configured to acquire patient physiological signals. Examples of such sensors include electrodes to detect ECG data, a perfusion sensor, a pulse oximeter, a Doppler device for detecting blood flow, a cuff for detecting blood pressure, an optical sensor, illumination detectors and perhaps sources for detecting color change in tissue, a motion sensor, a device that can detect heart wall movement, a sound sensor, a device with a microphone, an $SpO_2$ sensor, and so on. It will be appreciated that such sensors can help detect the patient's pulse, and can therefore also be called pulse detection sensors, pulse sensors, and pulse rate sensors. Pulse detection is also taught at least in Physio-Control's U.S. Pat. No. 8,135,462, which is hereby incorporated by reference in its entirety. In addition, a person skilled in the art may implement other ways of performing pulse detection. In such cases, the transducer includes an appropriate sensor, and the physiological input is a measurement by the sensor of that patient parameter. For example, the appropriate sensor for a heart sound may include a microphone, etc.

In some embodiments, the local parameter is a trend that can be detected in a monitored physiological parameter of patient 282. A trend can be detected by comparing values of parameters at different times. Parameters whose detected trends can particularly help a cardiac rehabilitation program include: a) cardiac function (e.g. ejection fraction, stroke volume, cardiac output, etc.); b) heart rate variability at rest or during exercise; c) heart rate profile during exercise and measurement of activity vigor, such as from the profile of an accelerometer signal and informed from adaptive rate pacemaker technology; d) heart rate trending; e) perfusion, such as from $SpO_2$ or $CO_2$; f) respiratory function, respiratory rate, etc.; g) motion, level of activity; and so on. Once a trend is detected, it can be stored and/or reported via a communication link, along perhaps with a warning. From the report, a physician monitoring the progress of patient 282 will know about a condition that is either not improving or deteriorating.

Patient state parameters include recorded aspects of patient 282, such as motion, posture, whether they have spoken recently plus maybe also what they said, and so on, plus optionally the history of these parameters. Or, one of these monitoring devices could include a location sensor such as a Global Positioning System (GPS) location sensor. Such a sensor can detect the location, plus a speed can be detected as a rate of change of location over time. Many motion detectors output a motion signal that is indicative of the motion of the detector, and thus of the patient's body. Patient state parameters can be very helpful in narrowing down the determination of whether SCA is indeed taking place.

A WCD system made according to embodiments may include a motion detector. In embodiments, a motion detector can be implemented within monitoring device 180 or monitoring device 281. Such a motion detector can be configured to detect a motion event. In response, the motion detector may render or generate from the detected motion event a motion detection input that can be received by a subsequent device or functionality. A motion event can be defined as is convenient, for example a change in motion from a baseline motion or rest, etc. Such a motion detector can be made in many ways as is known in the art, for example by using an accelerometer. In such cases, the patient parameter is a motion, one of the transducers may include a motion detector, and the physiological input is a motion measurement.

System parameters of a WCD system can include system identification, battery status, system date and time, reports of self-testing, records of data entered, records of episodes and intervention, and so on.

Environmental parameters can include ambient temperature and pressure. Moreover, a humidity sensor may provide information as to whether it is likely raining. Presumed patient location could also be considered an environmental parameter. The patient location could be presumed if monitoring device 180 or 281 includes a GPS location sensor as per the above.

Defibrillator 200 typically includes a defibrillation port 210, such as a socket in housing 201. Defibrillation port 210 includes electrical nodes 214, 218. Leads of defibrillation electrodes 204, 208, such as leads 105 of FIG. 1, can be plugged into defibrillation port 210, so as to make electrical contact with nodes 214, 218, respectively. It is also possible that defibrillation electrodes 204, 208 are connected continuously to defibrillation port 210, instead. Either way, defibrillation port 210 can be used for guiding, via electrodes, to the wearer the electrical charge that has been stored in an energy storage module 250 that is described more fully later in this document. The electric charge will be the shock for defibrillation, pacing, and so on.

Defibrillator 200 may optionally also have an ECG port 219 in housing 201, for plugging in sensing electrodes 209, which are also known as ECG electrodes and ECG leads. It is also possible that sensing electrodes 209 can be connected continuously to ECG port 219, instead. Sensing electrodes 209 are types of transducers that can help sense an ECG signal, e.g. a 12-lead signal, or a signal from a different number of leads, especially if they make good electrical contact with the body of the patient. Sensing electrodes 209 can be attached to the inside of support structure 170 for making good electrical contact with the patient, similarly as defibrillation electrodes 204, 208.

Optionally a WCD system according to embodiments also includes a fluid that it can deploy automatically between the electrodes and the patient skin. The fluid can be conductive, such as by including an electrolyte, for making a better electrical contact between the electrode and the skin. Electrically speaking, when the fluid is deployed, the electrical impedance between the electrode and the skin is reduced. Mechanically speaking, the fluid may be in the form of a low-viscosity gel, so that it does not flow away, after it has been deployed. The fluid can be used for both defibrillation electrodes 204, 208, and sensing electrodes 209.

The fluid may be initially stored in a fluid reservoir, not shown in FIG. 2, which can be coupled to the support structure. In addition, a WCD system according to embodiments further includes a fluid deploying mechanism 274. Fluid deploying mechanism 274 can be configured to cause at least some of the fluid to be released from the reservoir, and be deployed near one or both of the patient locations, to which the electrodes are configured to be attached to the patient. In some embodiments, fluid deploying mechanism 274 is activated prior to the electrical discharge responsive to receiving activation signal AS from processor 230 that is described more fully later in this document.

In some embodiments, defibrillator 200 also includes a transducer that includes a measurement circuit 220. Measurement circuit 220 senses one or more electrical physiological signal of the patient from ECG port 219, if provided. Even if defibrillator 200 lacks ECG port 219, measurement circuit 220 can obtain physiological signals through nodes 214, 218 instead, when defibrillation electrodes 204, 208 are attached to the patient. In these cases, the physiological input reflects an ECG measurement. The parameter can be an ECG, which can be sensed as a voltage difference between electrodes 204, 208. In addition, the parameter can be an impedance, which can be sensed between electrodes 204, 208 and/or the connections of ECG port 219. Sensing the impedance can be useful for detecting, among other things, whether these electrodes 204, 208 and/or sensing electrodes 209 are not making good electrical contact with the patient's body. These patient physiological signals can be sensed, when available. Measurement circuit 220 can then render or generate information about them as physiological inputs, data, other signals, etc. More strictly speaking, the information rendered by measurement circuit 220 is output from it, but this information can be called an input because it is received by a subsequent device or functionality as an input.

Defibrillator 200 also includes a processor 230. Processor 230 may be implemented in many ways. Such ways include, by way of example and not of limitation, digital and/or analog processors such as microprocessors and Digital Signal Processors (DSPs); controllers such as microcontrollers; software running in a machine; programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

The processor 230 may include, or have access to, a non-transitory storage medium, such as memory 238 that is described more fully later in this document. Such a memory can have a non-volatile component for storage of machine-readable and machine-executable instructions. A set of such instructions can also be called a program. The instructions, which may also be referred to as "software," generally provide for functionality by performing methods as may be disclosed herein or understood by one skilled in the art in view of the disclosed embodiments. In some embodiments, and as a matter of convention used herein, instances of the software may be referred to as a "module" and by other similar terms. Generally, a module includes a set of the instructions so as to offer or fulfill a particular functionality. Embodiments of modules and the functionality delivered are not limited by the embodiments described in this document.

Processor 230 can be considered to have a number of modules. One such module can be a detection module 232.

Detection module 232 can include a Ventricular Fibrillation (VF) detector. The patient's sensed ECG from measurement circuit 220, which can be available as physiological inputs, data, or other signals, may be used by the VF detector to determine whether the patient is experiencing VF. Detecting VF is useful, because VF results in SCA. Detection module 232 can also include a Ventricular Tachycardia (VT) detector, and so on.

Another such module in processor 230 can be an advice module 234, which generates advice for what to do. The advice can be based on outputs of detection module 232. There can be many types of advice according to embodiments. In some embodiments, the advice is a shock/no shock determination that processor 230 can make, for example via advice module 234. The shock/no shock determination can be made by executing a stored Shock Advisory Algorithm. A Shock Advisory Algorithm can make a shock/no shock determination from one or more of ECG signals that are captured according to embodiments, and determining whether a shock criterion is met. The determination can be made from a rhythm analysis of the captured ECG signal or otherwise.

In some embodiments, when the determination is to shock, an electrical charge is delivered to the patient. Delivering the electrical charge is also known as discharging. Shocking can be for defibrillation, pacing, and so on.

Processor 230 can include additional modules, such as other module 236, for other functions. In addition, if internal monitoring device 281 is indeed provided, it may be operated in part by processor 230, etc.

Defibrillator 200 optionally further includes a memory 238, which can work together with processor 230. Memory 238 may be implemented in many ways. Such ways include, by way of example and not of limitation, volatile memories, Nonvolatile Memories (NVM), Read-Only Memories (ROM), Random Access Memories (RAM), magnetic disk storage media, optical storage media, smart cards, flash memory devices, any combination of these, and so on. Memory 238 is thus a non-transitory storage medium. Memory 238, if provided, can include programs for processor 230, which processor 230 may be able to read and execute. More particularly, the programs can include sets of instructions in the form of code, which processor 230 may be able to execute upon reading. Executing is performed by physical manipulations of physical quantities, and may result in functions, operations, processes, actions and/or methods to be performed, and/or the processor to cause other devices or components or blocks to perform such functions, operations, processes, actions and/or methods. The programs can be operational for the inherent needs of processor 230, and can also include protocols and ways that decisions can be made by advice module 234. In addition, memory 238 can store prompts for user 282, if this user is a local rescuer. Moreover, memory 238 can store data. This data can include patient data, system data and environmental data, for example as learned by internal monitoring device 281 and outside monitoring device 180. The data can be stored in memory 238 before it is transmitted out of defibrillator 200, or stored there after it is received by defibrillator 200.

Defibrillator 200 may also include a power source 240. To enable portability of defibrillator 200, power source 240 typically includes a battery. Such a battery is typically implemented as a battery pack, which can be rechargeable or not. Sometimes a combination is used of rechargeable and non-rechargeable battery packs. Other embodiments of power source 240 can include an AC power override, for where AC power will be available, an energy storage capacitor, and so on. In some embodiments, power source 240 is controlled by processor 230. Appropriate components may be included to provide for charging or replacing power source 240.

Defibrillator 200 may additionally include an energy storage module 250. Energy storage module 250 can be coupled to the support structure of the WCD system, for example either directly or via the electrodes and their leads. Module 250 is where some electrical energy can be stored temporarily in the form of an electrical charge, when preparing it for discharge to administer a shock. In embodiments, module 250 can be charged from power source 240 to the right amount of energy, as controlled by processor 230. In typical implementations, module 250 includes a capacitor 252, which can be a single capacitor or a system of capacitors, and so on. In some embodiments, energy storage module 250 includes a device that exhibits high power density, such as an ultracapacitor. As described above, capacitor 252 can store the energy in the form of an electrical charge, for delivering to the patient.

Defibrillator 200 moreover includes a discharge circuit 255. When the decision is to shock, processor 230 can be configured to control discharge circuit 255 to discharge through the patient the electrical charge stored in energy storage module 250. When so controlled, circuit 255 can permit energy stored in module 250 to be discharged to nodes 214, 218, and from there also to defibrillation electrodes 204, 208, so as to cause a shock to be delivered to the patient. Circuit 255 can include one or more switches 257. Switches 257 can be made in a number of ways, such as by an H-bridge, and so on. In some embodiments, discharge circuit 255 is configurable to output multiphasic shocks, such as for example, biphasic shocks. In some embodiments, energy storage module has multiple distinct energy submodules (e.g., capacitors) and discharge circuit 255 is configurable to discharge a different energy storage submodule for each phase of a multiphasic shock. In some embodiments, circuit 255 can also be controlled via user interface 280.

Defibrillator 200 can optionally include a communication module 290, for establishing one or more wired or wireless communication links with other devices of other entities, such as a remote assistance center, Emergency Medical Services (EMS), and so on. Module 290 may also include such sub-components as may be deemed necessary by a person skilled in the art, for example an antenna, portions of a processor, supporting electronics, outlet for a telephone or a network cable, etc. This way, data, commands, etc. can be communicated. The data can include patient data, event information, therapy attempted, CPR performance, system data, environmental data, and so on. Defibrillator 200 in some embodiments can optionally include other components.

Returning to FIG. 1, in embodiments, one or more of the components of the shown WCD system have been customized for patient 82. This customization may include a number of aspects. For instance, support structure 170 can be fitted to the body of patient 82. For another instance, baseline physiological parameters of patient 82 can be measured, such as the heart rate of patient 82 while resting, while walking, motion detector outputs while walking, etc. Such baseline physiological parameters can be used to customize the WCD system, in order to make its diagnoses more accurate, since the patients' bodies differ from one another. Of course, such parameters can be stored in a memory of the WCD system, and so on.

A programming interface can be made according to embodiments, which receives such measured baseline physiological parameters. Such a programming interface may input automatically in the WCD system the baseline physiological parameters, along with other data.

Figure 3:
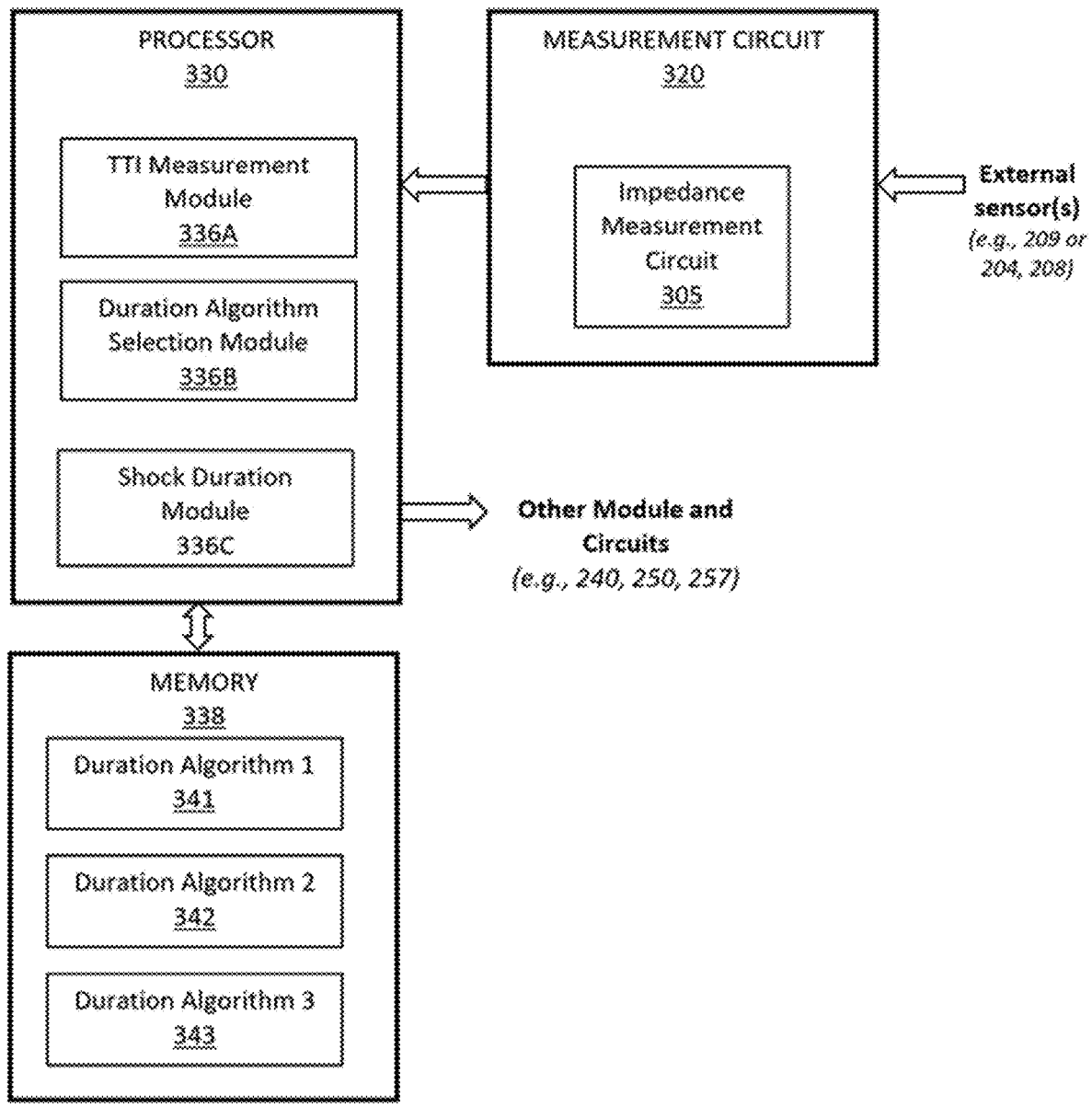
FIG. 3 is a diagram showing sample components of an external defibrillator similar to the external defibrillator of FIG. 2, in which some components are shown in more detail, according to embodiments.

FIG. 3 is a diagram showing sample components of an external defibrillator 301 similar to the external defibrillator 200 of FIG. 2, in which some components are shown in more detail, according to embodiments. External defibrillator 301 can be implemented in a WCD in some embodiments to deliver appropriate therapy (e.g., defibrillation shocks, cardioversion shocks, pacing, etc.) to a patient with an arrhythmia.

In this embodiment, external defibrillator 301 includes a measurement circuit 320 and memory 338, both coupled to a processor 330. External defibrillator 301 also includes other modules and components as shown in FIG. 2, but are omitted in FIG. 3 as they have already been described in detail in conjunction with FIG. 2.

Memory 338, in some embodiments, is similar to memory 238 (FIG. 2) and in addition is configured with at least two algorithms for determining the duration of a shock as a function of TTI. In FIG. 3, memory 338 is configured with three duration algorithms 341-343. In some embodiments, external defibrillator 301 is also configured so that no single shock can exceed a set duration. While some practitioners may not consider a fixed duration to be an "algorithm" in a technical sense, for purposes of this disclosure a maximum duration being used instead of a larger duration determined by another algorithm is a referred to herein as a Max Duration Waveform algorithm. In one embodiment, duration algorithms 341-343 are the Walcott Algorithm, the CE Algorithm, and the Max Duration algorithm, respectively. The Walcott Algorithm, CE Algorithm and the Max Duration Algorithms are described in more detail below. Further, in some embodiments, memory 338 is configured with at least two algorithms (not shown) for shaping the waveform of a shock to be delivered to a patient with the duration determined using duration algorithms such as described above. For example, the waveform algorithm can be a biphasic truncated exponential (BTE) waveform with equal duration phases, a biphasic truncated exponential waveform with the duration of the second phase being ⅔ of the first phase, rectilinear biphasic waveforms, biphasic square waveforms, pulsed waveforms, or waveforms with three or more phases. In some embodiments, the duration algorithm also defines the waveform such as, for example, the Walcott algorithm which defines the duration of each phase of a BTE waveform. Of course, other duration algorithms may also define the duration of each phase. In some embodiments, the external defibrillator is also configured with a minimum duration for the shock such as, for example, 4 ms.

In some embodiments, other algorithms can be used. For example, in some embodiments a modified version of the Walcott Algorithm can be used in which the shock duration is calculated in the same way as the original Walcott Algorithm but the periods of the waveform are modified (e.g., to be equal). Other algorithms include for example, monophasic truncated exponential algorithms, or algorithms based on a fixed duration or step-wise control of the duration for given range of TTI.

In addition, memory 338 can be configured with one or more voltage compensation algorithms (not shown) for determining a charge voltage for a capacitor energy storage module used in external defibrillator 301 to provide the energy for the shock. In some embodiments, the charge voltage of a capacitor used in external defibrillator 301 has a maximum voltage rating and known capacitance, which is accounted for in the voltage compensation algorithm. As will be described further below, in embodiments with the voltage compensation algorithm, external defibrillator 301 can deliver shocks with the desired energy to patients with higher TTIs than is typically delivered by external defibrillators with no voltage compensation.

In this embodiment, measurement circuit 320 is similar to measurement circuit 220 (FIG. 2), and more specifically shows an impedance measurement circuit 305 coupled to sensors coupled to the patient which are used in this embodiment to measure a patient's TTI. In some embodiments, impedance measurement circuit 305 provides a low voltage constant current AC signal (e.g., a series of pulses) to the patient via the sensors, such as described in U.S. Pat. No. 5,999,852 entitled "Defibrillator Method and Apparatus", which is incorporated herein by reference in its entirety. Impedance measurement circuit 305 can determine the TTI itself, or in other embodiments a TTI measurement module 336A of processor 330 determines the TTI.

Processor 330, in this embodiment, also includes a duration algorithm selection module 336B and a shock duration module 336C. Duration algorithm selection module 336B is configured to select between the duration algorithms configured in memory 338 based on the patient's measured TTI. In some embodiments, duration algorithm selection module 336B is configured to select between the duration algorithms 341-343 as a function of the measured patient TTI. For example, in some embodiments, one or more TTI thresholds are preset by an administrator, while in other embodiments the TTI thresholds are dynamically determined by processor 330 as a function of the measured patient TTI or the charge voltage in embodiments with voltage compensation and/or selectable shock energies. Duration algorithm selection module 336B then compares the measured TTI to the one or more thresholds. In some embodiments, if the measured TTI is below a first threshold, module 336B is configured to select Algorithm 1, and if the measured TTI is above the first threshold, module 336B is configured to select Algorithm 2. In embodiments with a third duration algorithm, a second threshold (higher than the first threshold) is determined or preset. If the measured TTI is above the second threshold, then module 336B is configured in this embodiment to select Algorithm 3.

In some other embodiments, processor 330 is configured to select the duration algorithm dynamically by determining the energies delivered by each of the algorithms and selecting the algorithm with the highest delivered energy (or the energy closest to the selected energy in some other embodiments).

Using the algorithm selected by module 336B, shock duration module 336C then determines the duration of the shock to be delivered to the patient, as a function of the measured TTI. In some embodiments, the shock is delivered in the form of a biphasic truncated exponential (BTE) waveform. In other embodiments, in addition to previously mentioned waveforms, other waveforms are used such as, for example, rectilinear biphasic waveforms, biphasic square waveforms, pulsed waveforms, or waveforms with three or more phases.

In some embodiments, in addition to controlling the duration of the shock, the charge voltage of the energy storage module (e.g., energy storage module 252 in FIG. 2) is controlled by processor 330 (or by processor 230 FIG. 2) as a function of patient TTI. This is sometimes referred to as voltage compensation. For example, in patients with relatively high TTI, for a given charge voltage, the energy delivered to the patient may not reach the desired level within the maximum duration. In these embodiments, the processor causes the energy storage module to be charged to a higher charge voltage for patients with relatively high TTI. This in effect causes the values of the first and second thresholds to increase (or move to the right in FIG. 4A, described below). As a result, more patients are likely to receive shocks with at least the CE Algorithm energy level. That is, this voltage compensation provides constant energy for patients with greater TTI than is achievable by duration compensation along. In some embodiments, the voltage compensation is performed in a step-wise manner based on the measured patient TTI. In other embodiments, the voltage compensation is performed in a continuous manner as a function of the measure patient TTI.

Figure 4A:
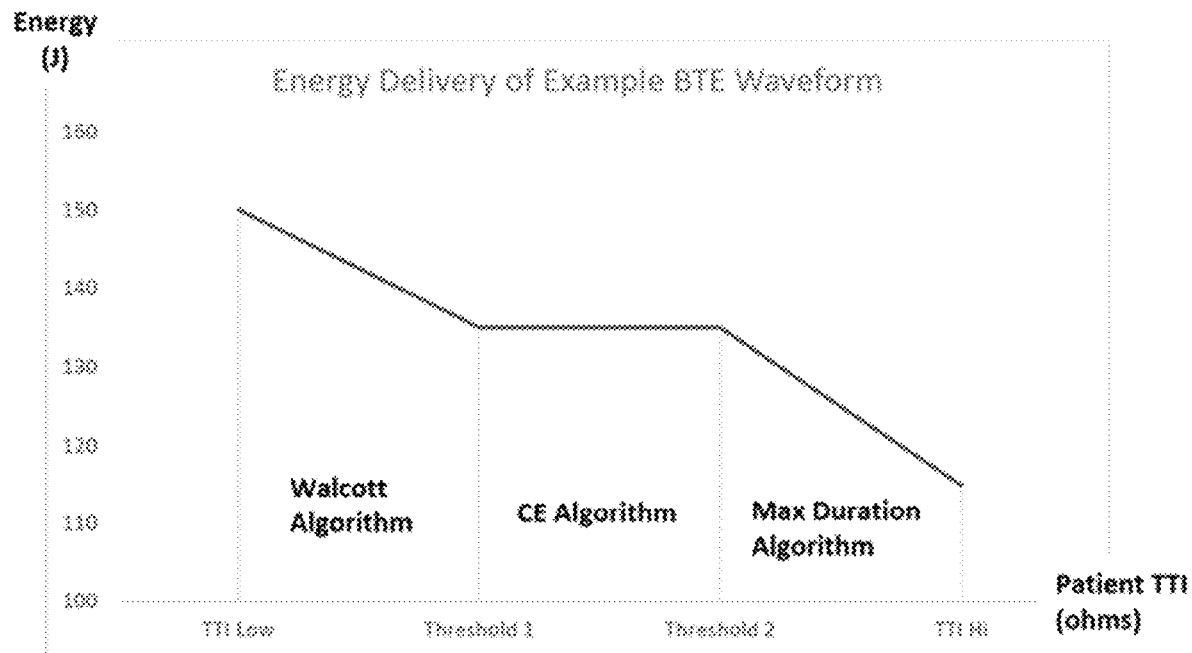
FIGS. 4A-4B are diagrams showing energy delivery of an example biphasic truncated exponential (BTE) waveform, according to embodiments.

FIG. 4A shows a chart illustrating an example of the thresholds and duration algorithms, according to embodiments. FIG. 4A shows energy (J) as a function of patient TTI (ohms). Note, the values for energy and TTI are illustrative for an example external defibrillator, and could be different for other defibrillators. In this example, for relatively low TTI (i.e., below Threshold 1), the Walcott Algorithm is selected (e.g., by duration selection module 336B in FIG. 3) to determine the shock duration. The durations of the Walcott algorithm result in shocks having energies that is inversely proportional to TTI. As can be seen in FIG. 4A, this results in a relatively high energy shock for low TTI patients ranging from about 150 J to about 135 J.

For "moderate" TTI patients (e.g., patients having a TTI between Threshold 1 and Threshold 2), the CE Algorithm is selected in this embodiment. As the name of the algorithm implies, such patients all receive the same energy, which in this example is about 135 J. This energy can be preset (for example, in a WCD or simple AEDs), or selectable by a user or rescuer (for example, via a user interface in external defibrillators designed for trained operators).

For "high" TTI patients (e.g., patients with TTI greater than Threshold 2), the Max Duration algorithm is selected in this embodiment. In some embodiments, the maximum duration of the shock according to the Max Duration Algorithm is preset in the external defibrillator by an administrator, physician, or in the factory when the external defibrillator is manufactured. In some embodiments, the maximum duration of the shock is less than 25 ms. As shown in FIG. 4A, using the Max Duration Algorithm, the energy delivered to the patient drops off as a function of patient TTI, reflecting that the delivered energy for a fixed duration decreases as TTI increases.

Figure 4B:
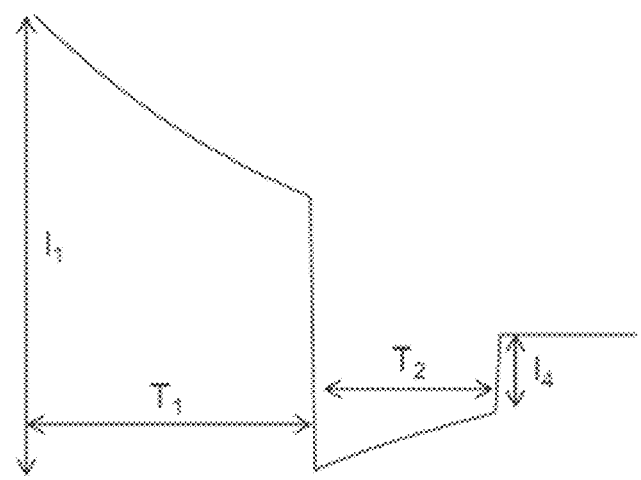

In addition to controlling total waveform duration, in embodiments using multiphasic shock waveforms, processor 330 also controls the relative proportion of the entire duration dedicated to the phases. FIG. 4B shows the phases of an example BTE waveform in terms of current (I) vs time (T). The duration of the first phase of the waveform is $T_1$, and with an initial current of $I_1$ that decays exponentially based on the patient's TTI and other resistances in the system such as from components in the external defibrillator and between the electrodes and the patient's skin. The second phase of the BTE waveform has a duration of $T_2$, and at the end of which the truncated waveform has a current of $I_4$.

In some embodiments, processor 330 is configured to control a single phase of the BTE waveform (relative duration) to improve defibrillation efficacy. For example, as shown in FIG. 4B, the BTE waveform has a total duration of $d=T_1+T_2$ where the relative duration of $T_1$ is $d_{1rel}=T_1/d$, and the relative duration of $T_2$ is $d_{2rel}=T_2/d$. In some embodiments, $d_{1rel}$ is a value between 0.3 and 0.7 and is fixed regardless of TTI. In other embodiments, the relative duration of each phase varies as TTI varies. In yet other embodiments $d_{1rel}$ is fixed in a given range or ranges of TTI while it varies in another range or ranges of TTI. These relative durations can be selected by an administrator, physician, etc., or preset when the external defibrillator is manufactured. These relative durations can be used to define waveform algorithms as previously described.

Walcott Algorithm

In the Walcott Algorithm, the total duration of the shock, d, is described by the equations below.

$$d = T_1 + 0.67 \cdot T_1 \forall R_{pt} < x \quad (1)$$

$$\text{where } T_1 = -\gamma \cdot \ln\left(\frac{\tau_m}{\tau_s}\right) \quad (2)$$

and $\tau_s$ and $\gamma$ are described by equations 3 and 4.

$$\tau_s = C_d \cdot (R_{pt} + R_d) \quad (3)$$

$$\gamma = \frac{\tau_s \cdot \tau_m}{\tau_s - \tau_m} \quad (4)$$

$C_d$ is the device capacitance, $R_d$ is the device impedance, $R_{pt}$ is the patient TTI, $\tau_m$ is the Walcott Model time constant and is between 4 and 8 ms, and x is a first threshold. In one embodiment, the first threshold is determined by the intercept of the energy delivery curves for the Walcott and CE Algorithms and the second threshold is determined by the TTI at which the device parameters (e.g., the capacitance of the energy storage module, the charge voltage, device impedances) can no longer deliver a shock with the energy set by the CE Algorithm In some embodiments, the Walcott Algorithm is modified so that the total duration d is the same (as in the original Walcott Algorithm), but the durations of the phases are slightly different. In one embodiment, the modified Walcott Algorithm has the phases being the same, as opposed to the second phase being 0.67 of the first phase as in the original Walcott Algorithm (see equation 1 above). In some embodiments, the modified Walcott Algorithm includes a minimum duration for the shock such as, for example, 4 ms.

Constant Energy (CE) Algorithm

Given the device configuration (capacitance, resistance, charge voltage), desired defibrillation energy, and measured patient impedance the following equation is used to calculate the total duration of the defibrillation waveform.

$$T_1 + T_2 = \frac{-\tau_s}{2} \cdot \ln\left(1 - \frac{E_{pt} \cdot (R_{pt} + R_d)}{0.5 \cdot R_{pt} \cdot V_{chg}^2 \cdot C_d}\right) \forall R_{pt} > x \quad (5)$$

where $T_1 + T_2$ is the total duration of the waveform and should not exceed approximately 25 ms or be less than 4 ms, $\tau_s$ is the time constant for the circuit consisting of the device and patient, $R_{pt}$ is the patient's measured TTI, $R_d$ is the device impedance, $E_{pt}$ is the target energy to be delivered to the patient, $V_{chg}$ is the charge voltage on the device capacitor, and $C_d$ is the device capacitance. In some embodiments, the CE algorithm is used only when $R_{pt}$ is greater than x, where x is the first threshold.

In accordance with this disclosure, external defibrillators can advantageously deliver effective shocks with greater energy to a wider range of patients than with any one waveform compensation technique alone, thereby maximizing the defibrillation efficacy. This disclosure can be especially advantageous in a defibrillator of limited energy storage capacity, such as a WCD.

The various embodiments of the devices and/or systems disclosed in this document perform functions, processes and/or methods as described above. These functions, processes and/or methods may be implemented by one or more devices that include logic circuitry. Such a device can be alternately called a computer, and so on. It may be a standalone device or computer, such as a general-purpose computer, or part of a device that has one or more additional functions. In some embodiments, the computer is a specialized computer adapted to and optimally configured for a specific purpose such as for example, providing therapy shocks in emergency situations. The logic circuitry may include a processor and non-transitory computer-readable storage media, such as memories, of the type described in this document. Often, for the sake of convenience, it is preferred to implement and describe a program as various interconnected distinct software modules or features. These, along with data are individually and also collectively referred to herein as software. In some instances, software is combined with hardware, in a mix called firmware.

Various embodiments of methods and algorithms are described below. These methods and algorithms are not necessarily inherently associated with any particular logic device or other apparatus. Rather, they can be advantageously implemented by programs for use by a computing machine, such as a general-purpose computer, a special purpose computer, a microprocessor, a microcontroller, a processor and/or a combination of these devices such as described elsewhere in this document, and so on.

This detailed description includes flowcharts, display images, algorithms, and symbolic representations of program operations within at least one computer readable medium. An economy is achieved in that a single set of flowcharts is used to describe both programs, and also methods. So, while flowcharts describe methods in terms of boxes, they also concurrently describe programs.

Figure 5:
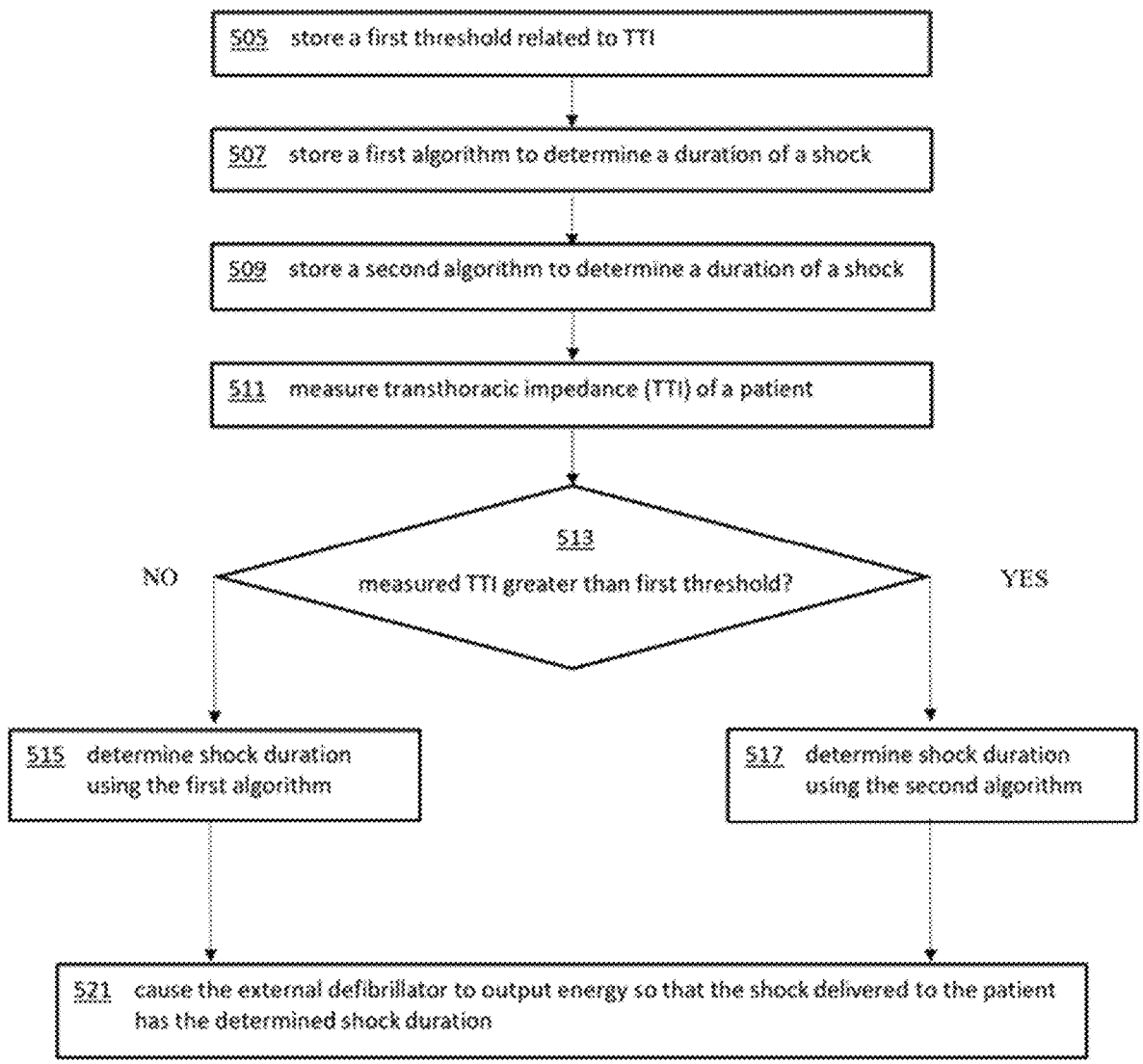
FIG. 5 is a flow diagram showing methods for determining shock duration, according to embodiments.

FIG. 5 is a flow diagram illustrating a method 500 for determining shock duration, according to embodiments. In an operation 505, a first threshold is stored. In some embodiments, the first threshold is stored in a memory of an external defibrillator such as for example, memory 238 (FIG. 2) or memory 338 (FIG. 3).

In an operation 507 and an operation 509, first and second algorithms for determining a duration of a shock are stored, respectively. In some embodiments, the algorithms are stored in a memory of an external defibrillator such as for example, memory 238 (FIG. 2) or memory 338 (FIG. 3). In some embodiments, the first algorithm is the Walcott Algorithm. In other embodiments, the first algorithm is a modified Walcott Algorithm. In some embodiments, the second algorithm is the CE Algorithm. In yet other embodiments, other duration algorithms or other modifications of the Walcott or CE Algorithms can be used for the first and second algorithms such as, for example, the previously mentioned constant duration, step-wise duration, and monophasic truncated exponential algorithms.

In an operation 511, the patient's TTI is measured. In some embodiments, the patient's TTI is measured via external sensors such as ECG or therapy electrodes (e.g., electrodes 204, 208, 209 in FIG. 2) by a measurement circuit of an external defibrillator such as, for example, measurement circuit 220 (FIG. 2) or impedance measurement circuit 305 in conjunction with TTI measurement module 336A (FIG. 3).

The duration of the shock is then determined based on the measured patient TTI. In some embodiments, the duration is determined by a processor of an external defibrillator such as, for example, processor 230 (FIG. 2) or processor 330 (FIG. 3). Embodiments of this process are described in more detail below.

In embodiments, in an operation 513, the measured TTI is analyzed or compared to determine if it is greater than the first threshold. In some embodiments, this determination is performed by a processor such as, for example, duration selection module 336B (FIG. 3) of processor 330.

If the measured TTI is not greater than (or not greater than or equal to in some embodiments) the first threshold, in an operation 515 the shock duration is determined using the first algorithm. In some embodiments, the first algorithm (per operation 507) is performed by a shock duration module such as, for example, shock duration module 336C of processor 330 (FIG. 3).

If the measured TTI is greater than (or greater than or equal to in some embodiments) the first threshold, in an operation 517 the shock duration is determined using the second algorithm. In some embodiments, the second algorithm (per operation 509) is performed by a shock duration module such as, for example, shock duration module 336C of processor 330 (FIG. 3).

In an operation 521, the external defibrillator is caused to output a shock with the duration determined in operation 515 or 517, depending on the measured patient TTI. In some embodiments, this operation is performed by a processor of an external defibrillator such as, for example, processor 230 (FIG. 2) or processor 330 (FIG. 3), controlling other components of the external defibrillator (e.g., as described above in conjunction with FIGS. 2 and 3).

Figure 6:
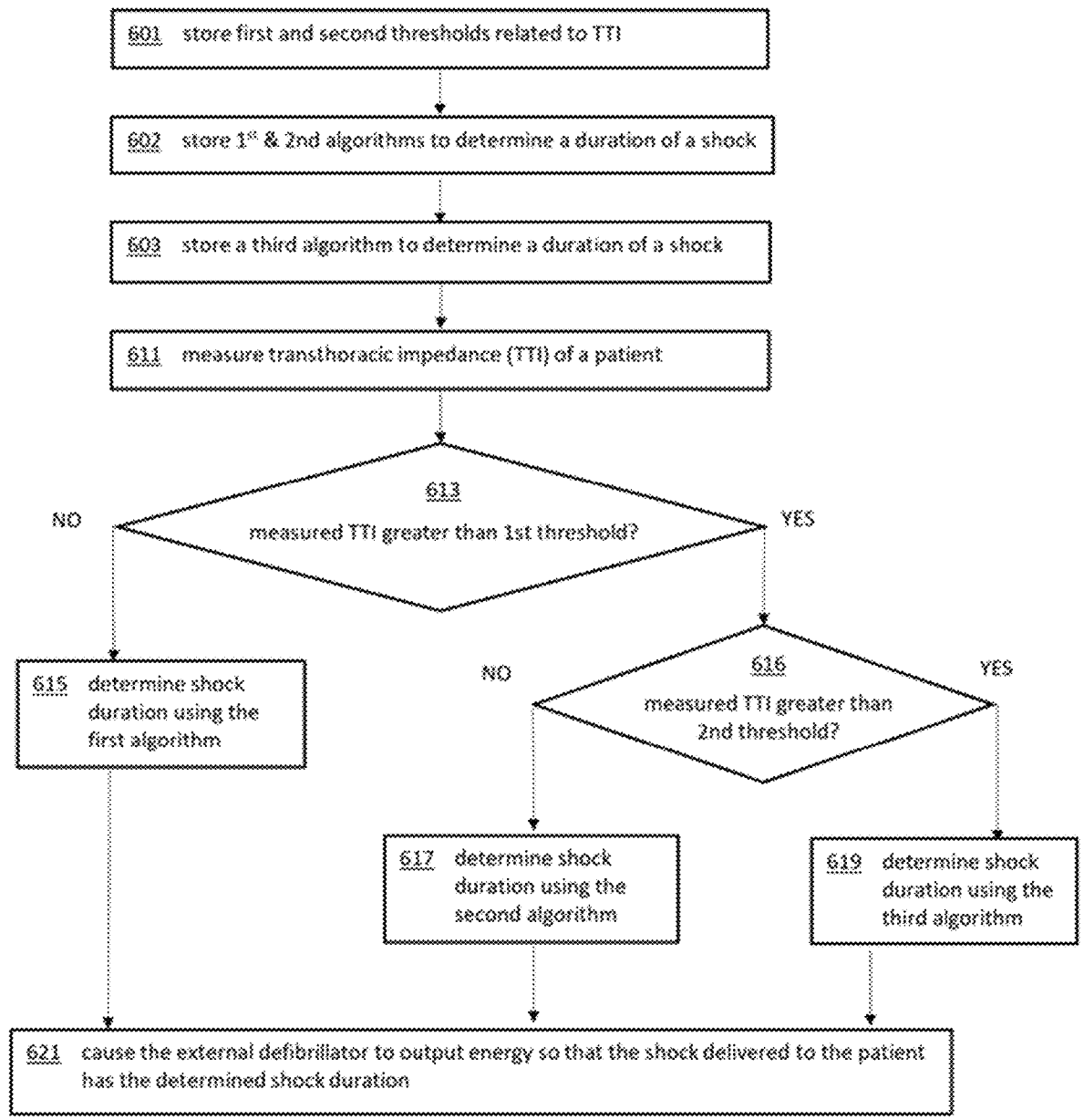
FIG. 6 is a flow diagram showing additional methods for determining shock duration, according to embodiments.

FIG. 6 is a flow diagram illustrating a method 600 for determining shock duration, according to embodiments. In an operation 601, a first threshold and a second threshold are stored. In some embodiments, the first and second thresholds are stored in a memory of an external defibrillator such as for example, memory 238 (FIG. 2) or memory 338 (FIG. 3).

In an operation 602, first and second algorithms for determining a duration of a shock are stored. In some embodiments, the algorithms are stored in a memory of an external defibrillator such as for example, memory 238 (FIG. 2) or memory 338 (FIG. 3). In some embodiments, the first algorithm is the Walcott Algorithm. In other embodiments, the first algorithm is a modified Walcott Algorithm. In some embodiments, the second algorithm is the CE Algorithm. In yet other embodiments, other duration algorithms or other modifications of the Walcott or CE Algorithms can be used for the first and second algorithms such as, for example, the previously mentioned constant duration, step-wise duration, and monophasic truncated exponential algorithms.

In an operation 603, a third algorithm for determining a duration of a shock is stored. In some embodiments, the algorithm is stored in the same memory as described above in conjunction with operation 602. In some embodiments, the third algorithm is the previously described Max Duration Algorithm. In other embodiments, other duration algorithms or modifications of the Walcott or CE or Max Duration Algorithms are used for the third algorithm.

In an operation 611, the patient's TTI is measured. In some embodiments, the patient's TTI is measured via external sensors such as ECG or therapy electrodes (e.g., electrodes 204, 208, 209 in FIG. 2) by a measurement circuit of an external defibrillator such as, for example, measurement circuit 220 (FIG. 2) or impedance measurement circuit 305 in conjunction with TTI measurement module 336A (FIG. 3).

The duration of the shock is then determined based on the measured patient TTI, in embodiments. In some embodiments, the duration is determined by a processor of an external defibrillator such as, for example, processor 230 (FIG. 2) or processor 330 (FIG. 3). Embodiments of this process are described in more detail below.

In embodiments, in an operation 613, the measured TTI is analyzed or compared to determine if it is greater than the first threshold. In some embodiments, this determination is performed by a processor such as, for example, duration selection module 336B (FIG. 3) of processor 330.

If the measured TTI is not greater than (or not greater than or equal to in some embodiments) the first threshold, in an operation 615 the shock duration is determined using the first algorithm. In some embodiments, the first algorithm (per operation 602) is performed by a shock duration module such as, for example, shock duration module 336C of processor 330 (FIG. 3).

If the measured TTI is greater than (or greater than or equal to in some embodiments) the first threshold, in an operation 616 the measured TTI is analyzed or compared to determine if it is greater than the second threshold. In some embodiments, this determination is performed by the processor as described above in conjunction with operation 613.

If the measured TTI is not greater than (or not greater than or equal to in some embodiments) the second threshold, in an operation 617 the shock duration is determined using the second algorithm. In some embodiments, the second algorithm (per operation 602) is performed by a shock duration module such as, for example, shock duration module 336C of processor 330 (FIG. 3).

If the measured TTI is greater than (or greater than or equal to in some embodiments) the second threshold, in an operation 619 the shock duration is determined using the third algorithm. In some embodiments, the third algorithm (per operation 603) is performed by a shock duration module such as, for example, shock duration module 336C of processor 330 (FIG. 3).

In an operation 621, the external defibrillator is caused to output a shock with the duration determined in operation 615 or 617 or 619, depending on the measured patient TTI. In some embodiments, this operation is performed by a processor of an external defibrillator such as, for example, processor 230 (FIG. 2) or processor 330 (FIG. 3), controlling other components of the external defibrillator (e.g., as described above in conjunction with FIGS. 2 and 3).

Figure 7:
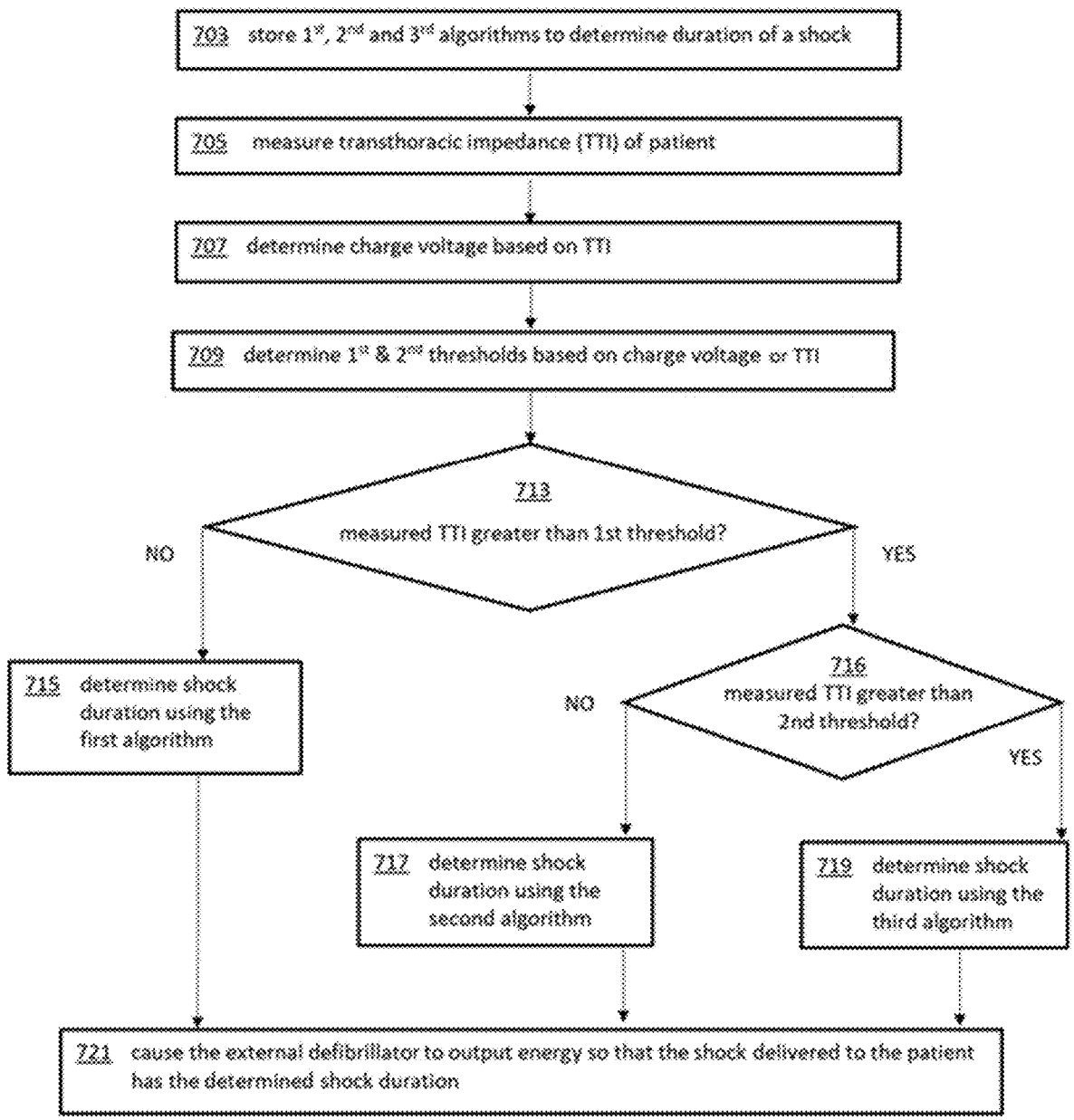
FIG. 7 is a flow diagram showing methods for determining charge voltage and shock duration, according to embodiments.

FIG. 7 is a flow diagram illustrating a method 700 for determining charge voltage and shock duration, according to embodiments. In an operation 703, first, second and third algorithms for determining a duration of a shock are stored. In some embodiments, the algorithms are stored in a memory of an external defibrillator such as for example, memory 238 (FIG. 2) or memory 338 (FIG. 3). In some embodiments, the first algorithm is the Walcott Algorithm. In other embodiments, the first algorithm is a modified Walcott Algorithm. In some embodiments, the second algorithm is the CE Algorithm. In some embodiments, the third algorithm is the Max Duration Algorithm In yet other embodiments, other duration algorithms or other modifications of the Walcott or CE or Max Duration Algorithms can be used for the first, second and third algorithms such as, for example, the previously mentioned constant duration, step-wise duration, and monophasic truncated exponential algorithms.

In an operation 705, the patient's TTI is measured. In some embodiments, the patient's TTI is measured via external sensors such as ECG or therapy electrodes (e.g., electrodes 204, 208, 209 in FIG. 2) by a measurement circuit of an external defibrillator such as, for example, measurement circuit 220 (FIG. 2) or impedance measurement circuit 305 in conjunction with TTI measurement module 336A (FIG. 3).

In an operation 707, a charge voltage is determined based on the measured patient TTI. In some embodiments, the charge voltage is determined by a processor of an external defibrillator such as, for example, processor 230 (FIG. 2) or processor 330 (FIG. 3) using a voltage compensation algorithm. In some embodiments, the voltage compensation algorithm increases the charge voltage of an energy storage module such as, for example, energy storage module 250 (FIG. 2), and the processor then causes an energy storage module of the external defibrillator to be charged to the determined voltage. In some embodiments, the voltage compensation algorithm increases the charge voltage as a step-wise function of measured patient TTI, and in other embodiments as a continuous function of measured patient TTI.

In an operation 709, a first threshold and a second threshold are determined. In some embodiments, the first and second thresholds are determined by a processor such as described above in conjunction with operation 707 as a function of the charge voltage and/or measured patient TTI. In some embodiments, the determined first and second threshold are then stored in a memory of an external defibrillator such as for example, memory 238 (FIG. 2) or memory 338 (FIG. 3).

The duration of the shock is then determined based on the measured patient TTI, in embodiments. In some embodiments, the duration is determined by a processor of an external defibrillator such as, for example, processor 230 (FIG. 2) or processor 330 (FIG. 3). Embodiments of this process are described in more detail below.

In embodiments, in an operation 713, the measured TTI is analyzed or compared to determine if it is greater than the first threshold. In some embodiments, this determination is performed by a processor such as, for example, duration selection module 336B (FIG. 3) of processor 330.

If the measured TTI is not greater than (or not greater than or equal to in some embodiments) the first threshold, in an operation 715 the shock duration is determined using the first algorithm. In some embodiments, the first algorithm (per operation 703) is performed by a shock duration module such as, for example, shock duration module 336C of processor 330 (FIG. 3).

If the measured TTI is greater than (or greater than or equal to in some embodiments) the first threshold, in an operation 716 the measured TTI is analyzed or compared to determine if it is greater than the second threshold. In some embodiments, this determination is performed by the processor as described above in conjunction with operation 713.

If the measured TTI is not greater than (or not greater than or equal to in some embodiments) the second threshold, in an operation 717 the shock duration is determined using the second algorithm. In some embodiments, the second algorithm (per operation 703) is performed by a shock duration module such as, for example, shock duration module 336C of processor 330 (FIG. 3).

If the measured TTI is greater than (or greater than or equal to in some embodiments) the second threshold, in an operation 719 the shock duration is determined using the third algorithm. In some embodiments, the third algorithm (per operation 703) is performed by a shock duration module such as, for example, shock duration module 336C of processor 330 (FIG. 3).

In an operation 721, the external defibrillator is caused to output a shock with the duration determined in operation 715 or 717 or 719, depending on the measured patient TTI. In some embodiments, this operation is performed by a processor of an external defibrillator such as, for example, processor 230 (FIG. 2) or processor 330 (FIG. 3), controlling other components of the external defibrillator (e.g., as described above in conjunction with FIGS. 2 and 3).

Time to Ratio (UR) Embodiments

Figure 8:
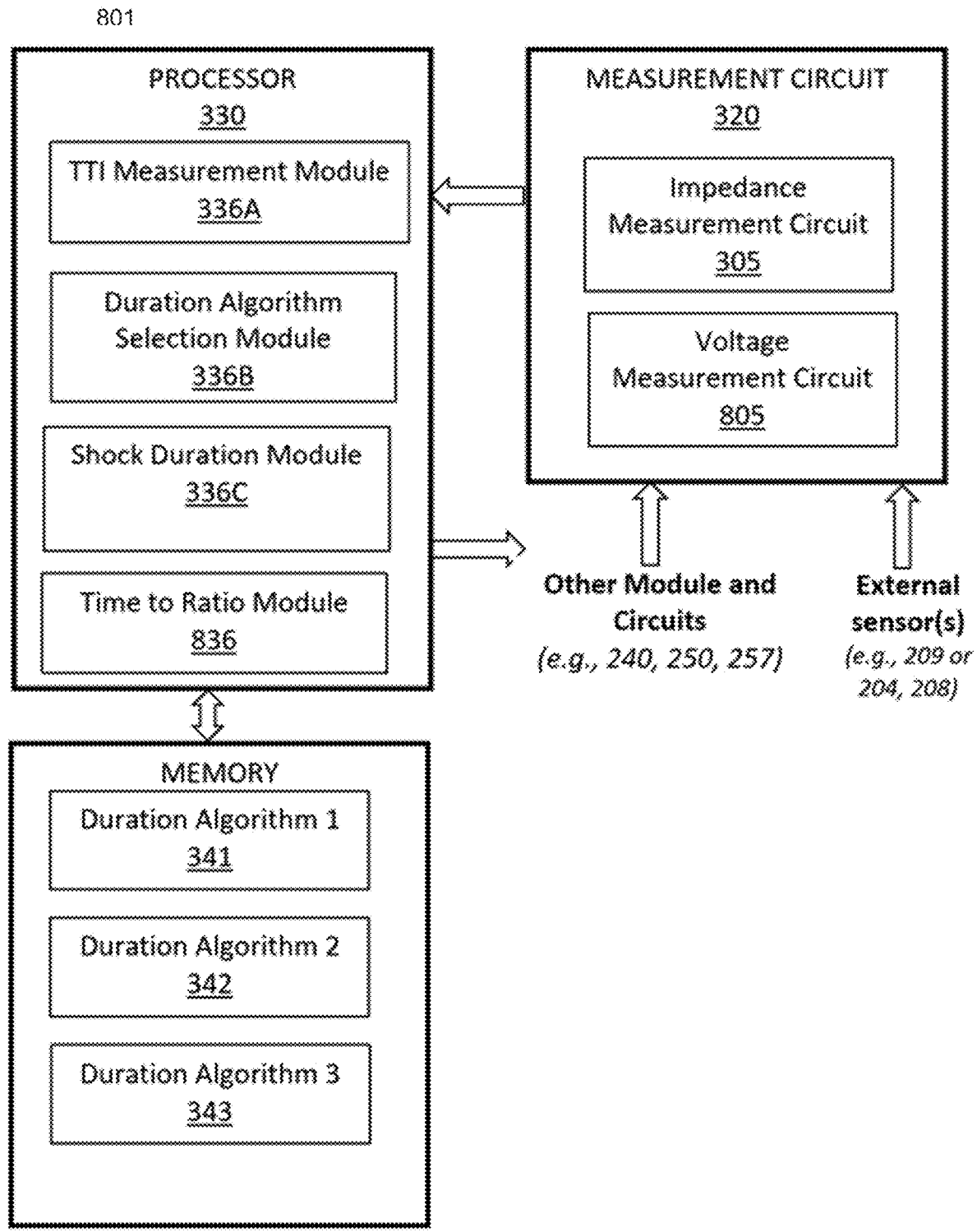
FIG. 8 is a diagram showing sample components of an external defibrillator similar to the external defibrillator of FIGS. 2 and 3, in which some components are shown in more detail, according to embodiments.

FIG. 8 is a diagram showing sample components of an external defibrillator 801 similar to external defibrillator 200 (FIG. 2) and external defibrillator 301 (FIG. 3), in which some components are shown in more detail, according to embodiments. External defibrillator 801 can be implemented in a WCD in some embodiments to deliver appropriate therapy (e.g., defibrillation shocks, cardioversion shocks, pacing, etc.) to a patient with an arrhythmia.

In this embodiment, external defibrillator 801 includes measurement circuit 320, memory 338, and processor 330 as described above in conjunction with FIG. 3, and other modules and components as shown in FIG. 2 (but omitted in FIG. 8 as they have already been described in detail in conjunction with FIG. 2).

Memory 338 of external defibrillator 801, in some embodiments, is similar to memory 338 (FIG. 3), being configured with at least two duration algorithms such as for example, the Walcott Algorithm, the Mod-cott Algorithm, the CE Algorithm or the previously described Max Duration Algorithm. In some embodiments, the duration algorithms include a minimum duration (e.g., 4 ms) for the shock. In addition, in some embodiments memory 338 is configured with at least one algorithm (not shown) for shaping (e.g., determining the durations of each phase of a multiphasic waveform) the waveform of a shock to be delivered to a patient. In some embodiments, the waveform is a BTE waveform with equal phases. In other embodiments, the waveform is a multiphasic waveform with one phase being an exponential, and another phase being a rectilinear. In some embodiments, the phase durations of a multiphasic exponential waveform are configured in a similar manner as described above in conjunction with FIG. 4B. In some embodiments, one or more of the duration algorithms also define the waveform (e.g., the duration of each phase of a BTE waveform as defined by the Walcott or equal phase Mod-cott duration algorithms).

In this embodiment, measurement circuit 320 is similar to measurement circuit 320 (FIG. 3), and more specifically also shows a voltage measurement circuit 805 coupled to the energy storage module such as, for example, energy storage module 250 (FIG. 2). In some embodiments, voltage measurement circuit 505 measures the charge voltage of a capacitor of the energy storage module while a shock is being administered to the patient.

Processor 330 of external defibrillator 801, in some embodiments, is similar to processor 330 (FIG. 3) and in addition includes a Time To Ratio (TTR) module 836. In some embodiments, TTR module 836 is configured to determine the time it takes a fully charged energy storage module to discharge to a selected voltage ratio (also referred to as the decay time). For example, in some embodiments, the ratio is 82% of the peak voltage. The decay time needed to discharge to the set voltage ratio can then be used to calculate the durations according to the first and second duration algorithms 342 and 342 as described below.

In general, the decay time $\tau_1$ for a ratio of 82% can be calculated according to equation (6) below.

$$\tau_1 = C_d \cdot (R_{pt} + R_d) \cdot \ln(0.82) \tag{6}$$

where the capacitance and resistances are defined as in equation (3) above. In this embodiment, the patient TTI is not measured and instead TTR module 836 measures $\tau_1$ during delivery of the shock. But as can be seen in equation (6), patients with a relatively low TTI will have a lower decay time $\tau_1$ than patients with a relatively high TTI.

In one embodiment, duration algorithm 341 of FIG. 8 is configured to determine the duration $D_{MC}$ of a Mod-Cott (modified Walcott) waveform using the measured $\tau_1$ according to equation (7) below. In one embodiment, the Mod-Cott waveform is the same as the Walcott waveform except that it has phases of equal duration.

$$D_{MC} = \frac{5}{3}\left(\left(\left(\left(\frac{-\tau_1}{\ln(0.82)}\right) \cdot \tau_m\right) \div \left(\left(\frac{-\tau_1}{\ln(0.82)}\right) - \tau_m\right)\right) \cdot \ln\left(\frac{\tau_m}{\frac{-\tau_1}{\ln(0.82)}}\right)\right) \tag{7}$$

where $\tau_m$ is the Walcott Model time constant and in in this embodiment is 0.0051. In other embodiments, other duration algorithms based on TTI can be mathematically recast as a function the decay time $\tau_1$ instead of TTI by one skilled in the art after review of this disclosure.

In some embodiments, duration algorithm 342 of FIG. 8 is configured to determine the duration $D_{CE}$ of a CE algorithm waveform as a function of the measured decay time $\tau_1$ instead of measured patient TTI. In some embodiments, equation (5) above is solved to be a function of a UR of 82%. For this UR, it can be shown that for a nominal 150 J Constant Energy waveform sourced from a 138 μF capacitor charged to 1600 volts, the duration $D_{CE}$ can be determined as a function of the measured $\tau_1$ according to equation (8) below.

$$D_{CE} = 6.13 \cdot \tau_1 \tag{8}$$

In other embodiments, different shock energies, capacitances, and/or charge voltage will result in the measured decay time $\tau_1$ being multiplied by a different constant.

In some embodiments, the capacitance of a nominally 138 μF energy storage module is calibrated. In such embodiments, the duration $D_{CE}$ can be determined as a function of the measured $\tau_1$ according to equation (9) below.

$$D_{CE} = (6.13 \cdot \tau_1) \bigg/ \left(\frac{Ccal}{138 \, \mu F}\right) \tag{9}$$

where Ccal is the actual capacitance measured during calibration.

In some embodiments, processor 330 of FIG. 8 then compares the durations determined using the first and second duration algorithms, and selects the algorithm having the larger duration. In one embodiment, TTR module 836 performs this selection. Using the selected algorithm, processor 330 of FIG. 8, then controls the discharge circuit (e.g., discharge circuit 255 of FIG. 2) so that the shock delivered to the patient has the waveform associated with the selected duration algorithm. In some embodiments where the first duration algorithm is the Walcott algorithm and the second waveform algorithm is the CE duration algorithm, the selection of the duration algorithm somewhat follows the graph of FIG. 4A in that relatively low decay times will result in selection of the Walcott algorithm and a moderate decay time will result in the selection of the CE algorithm. In some embodiments, both duration algorithms are associated with a BTE waveform having equal duration phases. In other embodiments, the duration algorithm may each be associated with a waveform algorithm with different phase durations, different types of waveforms (e.g., exponential versus rectilinear), different number of phases, or even with specific phases having shapes according to different types of waveforms (e.g., first phase being rectilinear and a second phase being exponential).

Figure 9:
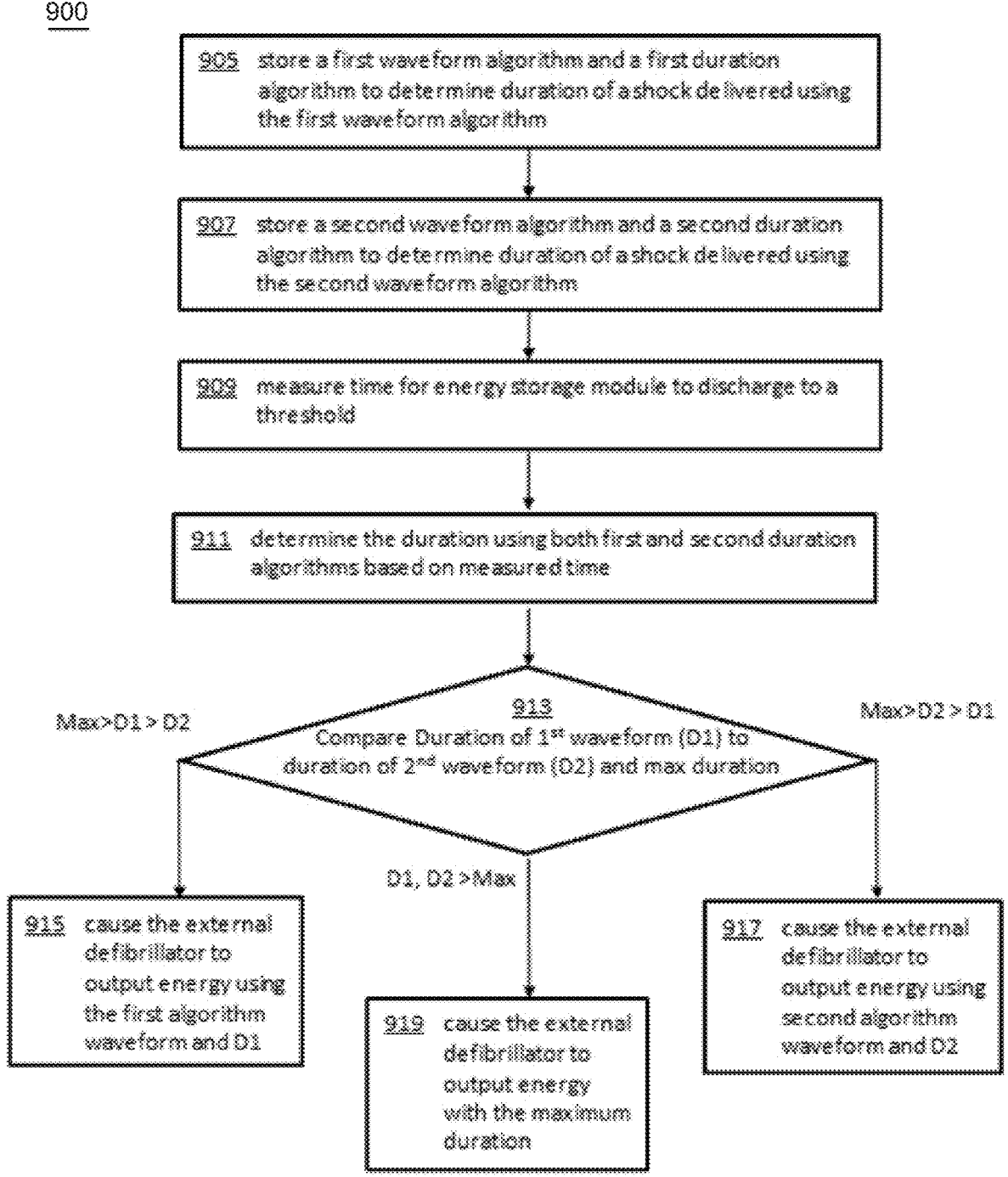
FIG. 9 is a flow diagram showing additional methods for determining shock duration and selecting a shock waveform, according to embodiments.

FIG. 9 is a flow diagram illustrating a method 900 for selecting a shock duration based on TTR, according to embodiments. In an operation 905, a first waveform algorithm and a first duration algorithm are stored. In some embodiments a single algorithm may define both a duration and waveform (e.g., the Walcott Algorithm). In some embodiments, the first waveform algorithm is for delivering a shock having Walcott waveform (i.e., a BTE waveform with the second phase having a duration that is ⅔ of the first phase) and first duration algorithm is for determining the duration the Walcott waveform as a function of measured decay time (i.e., the Walcott Algorithm as a function of TTR). In some other embodiments, the Mod-cott waveform algorithm is used instead of the Walcott waveform algorithm. In some embodiments, these waveforms are stored in a memory of an external defibrillator such as for example, memory 338 (FIG. 8).

In an operation 907, a second waveform algorithm and a second duration algorithm are stored. In some embodiments, the second waveform algorithm is for delivering a shock having an equal phase duration BTE waveform and second duration algorithm is for determining the duration the CE waveform as a function of measured decay time (i.e., the CE Algorithm as a function of TTR). In some embodiments, if the determined duration exceeds a predetermined or selected maximum, the duration is then set to this maximum. In some embodiments, these waveform algorithms are stored in a memory of an external defibrillator such as for example, memory 338 (FIG. 8). As stated earlier in operation 905, the waveform algorithm may be the same as the duration algorithm (e.g., the Mod-cott Algorithm can define both the total duration and the duration of each phase of a BTE waveform). In some embodiments, while durations algorithms 1 and 2 are different, the waveform algorithms may be the same (e.g., a BTE waveform with equal phases). In yet other embodiments, other waveform and duration algorithms or other modifications of the Walcott or CE Algorithms can be used for the first and second waveform and duration algorithms such as, for example, monophasic truncated exponential algorithms.

In an operation 909, a delivery of a shock to the patient is initiated and the decay to reach a selected or set ratio measured. In some embodiments, the ratio is 82%. In other embodiments, the ratio can be different within the range from about 80% to about 99%, and so that there is still time to control the shock to have a waveform according to both first and second waveform algorithms. For example, if the ratio is too low (meaning more time is needed to discharge to that lower percentage) it might be that the discharge is past the time for ending the first phase of one of the waveform algorithms, especially as described below, some additional time may be needed to determine durations using both the first and second algorithms. If the ratio is too high, the decay time measurement might be less accurate. In some embodiments, this operation is performed by a processor of an external defibrillator such as, for example, TTR module 836 of processor 330 (FIG. 8), controlling and/or receiving measurements from other components of the external defibrillator (e.g., as described above in conjunction with FIGS. 2, 3 and 8).

In an operation 911, the first and second duration algorithms are executed to determine durations of the waveforms according to the first and second waveform algorithms. In some embodiments, shock duration module 336C of processor 330 (FIG. 8) determines these durations.

In embodiments, in an operation 913, the determined durations are analyzed or compared, including comparing to a maximum duration in some embodiments For example, the maximum duration is set to a value below 25 ms (e.g., 22 ms) in one embodiment. In some embodiments, the determined durations are also compared to a minimum duration (e.g., 4 ms). In some embodiments, these determinations are performed by a processor such as, for example, processor 330 (FIG. 8). In some embodiments, this determination is in particular performed by TTR module 836 and/or duration selection module 336B of processor 330 (FIG. 8).

If the determined duration of the waveform according to waveform algorithm 1 (i.e., duration D1) is greater than (or greater than or equal to in some embodiments) the determined duration of the waveform according to waveform algorithm 2 (i.e. duration D2), in an operation 915 the external defibrillator is controlled to deliver energy according to waveform algorithm 1 with duration D1. In some embodiments, waveform algorithm 1 produces a BTE waveform with each phase having the same duration. In some embodiments, this operation is performed by a processor of the external defibrillator such as, for example, processor 330 (FIG. 8), controlling other components of the external defibrillator (e.g., as described above in conjunction with FIGS. 2, 3 and 8).

In other embodiments configured with a selected or predetermined minimum duration, if in addition duration D1 is greater than the minimum duration, then operation 915 is performed as described above. However, if the determined duration is less than the minimum duration, then the algorithm sets the duration to this minimum duration and causes the external defibrillator to deliver a shock to the patient according to waveform algorithm 1 having the minimum duration. In other embodiments the minimum duration waveform is another waveform different from that produced by waveform algorithm 1.

However, if duration D1 is not greater than (or not greater than or equal to in some embodiments) duration D2, in an operation 917 the external defibrillator is controlled to deliver energy according to waveform algorithm 2 with duration D2. In some embodiments, waveform algorithm 2 also produces a BTE waveform with each phase having the same duration. In other embodiments, waveform algorithm 2 produces a different waveform than waveform algorithm 1. In embodiments configured with a maximum duration, if in addition duration D2 is less than the maximum duration, operation 917 is performed as previously described. In some embodiments, this determination is performed by the processor as described above in conjunction with operation 915.

In embodiments configured with a maximum duration, responsive to both durations D1 and D2 exceeding the maximum duration, in an operation 919 the external defibrillator is controlled to deliver energy with the maximum duration (e.g., the previously described Max Duration Algorithm). In some embodiments, the waveform is a BTE waveform with equal duration phases. In some embodiments, the waveform algorithms 1-3 are all the same in that they cause the shock to have a BTE waveform with equal duration phases. In the methods described above, each operation can be performed as an affirmative step of doing, or causing to happen, what is written that can take place. Such doing or causing to happen can be by the whole system or device, or just one or more components of it. After review of this disclosure, a person of skill in the art will recognize that the methods and the operations may be implemented in many ways, including using systems, devices and implementations described above. In addition, the order of operations is not constrained to what is shown, and different orders may be possible according to different embodiments. Examples of such alternate orderings may include overlapping, interleaved, interrupted, reordered, incremental, preparatory, supplemental, simultaneous, reverse, or other variant orderings, unless context dictates otherwise. Moreover, in certain embodiments, new operations may be added, or individual operations may be modified or deleted. The added operations can be, for example, from what is mentioned while primarily describing a different system, apparatus, device or method.

A person skilled in the art will be able to practice the present invention in view of this description, which is to be taken as a whole. Details have been included to provide a thorough understanding. In other instances, well-known aspects have not been described, in order to not obscure unnecessarily this description. Plus, any reference to any prior art in this description is not, and should not be taken as, an acknowledgement or any form of suggestion that such prior art forms parts of the common general knowledge in any country or any art.

This description includes one or more examples, but this fact does not limit how the invention may be practiced. Indeed, examples, instances, versions or embodiments of the invention may be practiced according to what is described, or yet differently, and also in conjunction with other present or future technologies. Other such embodiments include combinations and sub-combinations of features described herein, including for example, embodiments that are equivalent to the following: providing or applying a feature in a different order than in a described embodiment; extracting an individual feature from one embodiment and inserting such feature into another embodiment; removing one or more features from an embodiment; or both removing a feature from an embodiment and adding a feature extracted from another embodiment, while providing the features incorporated in such combinations and sub-combinations.

In general, the present disclosure reflects preferred embodiments of the invention. The attentive reader will note, however, that some aspects of the disclosed embodiments extend beyond the scope of the claims. To the respect that the disclosed embodiments indeed extend beyond the scope of the claims, the disclosed embodiments are to be considered supplementary background information and do not constitute definitions of the claimed invention.

In this document, depending on the context, the phrases "constructed to" and/or "configured to" denote one or more actual states of construction and/or configuration that is fundamentally tied to physical characteristics of the element or feature preceding these phrases and, as such, reach well beyond merely describing an intended use. Any such elements or features can be implemented in many ways, by a person skilled in the art after reviewing the present disclosure, beyond any examples shown in this document.

All parent, grandparent, great-grandparent, etc. patent applications, whether mentioned in this document or in an Application Data Sheet ("ADS") of this patent application, are hereby incorporated by reference herein as originally disclosed, including any priority claims made in those applications and any material incorporated by reference, to the extent such subject matter is not inconsistent herewith.

In this description, a single reference numeral may be used consistently to denote a single item, aspect, component, or process. Moreover, a further effort may have been made in the drafting of this description to use similar though not identical reference numerals to denote other versions or embodiments of an item, aspect, component or process that are identical or at least similar or related. Where made, such a further effort was not required, but was nevertheless made gratuitously to accelerate comprehension by the reader. Even where made in this document, such a further effort might not have been made completely consistently for all of the versions or embodiments that are made possible by this description. Accordingly, the description controls in defining an item, aspect, component or process, rather than its reference numeral. Any similarity in reference numerals may be used to infer a similarity in the text, but not to confuse aspects where the text or other context indicates otherwise.

This disclosure is meant to be illustrative and not limiting on the scope of the following claims. The claims of this document define certain combinations and subcombinations of elements, features and steps or operations, which are regarded as novel and non-obvious. Additional claims for other such combinations and subcombinations may be presented in this or a related document. These claims are intended to encompass within their scope all changes and modifications that are within the true spirit and scope of the subject matter described herein. The terms used herein, including in the claims, are generally intended as "open" terms. For example, the term "including" should be interpreted as "including but not limited to," the term "having" should be interpreted as "having at least," etc. If a specific number is ascribed to a claim recitation, this number is a minimum but not a maximum unless stated otherwise. For example, where a claim recites "a" component or "an" item, it means that it can have one or more of this component or item.

What is claimed is:

1. An external defibrillator, comprising:
    two or more electrodes configured to contact a patient;
    an energy storage module;
    a discharge circuit coupled with the energy storage module and at least two of the two or more electrodes;
    an impedance measuring circuit; and
    one or more processors coupled to control the impedance measuring circuit and the discharge circuit, wherein the one or more processors are configured to:
        measure a transthoracic impedance (TTI) of the patient using the impedance measuring circuit; and
    cause the discharge circuit to apply a shock having a first phase duration and a second phase duration to the patient using the at least two of the two or more electrodes, wherein:
        when the TTI is below a predetermined TTI value, a first algorithm is used to determine the first and second phase durations, wherein the first phase duration is equal to the second phase duration; and
        when the TTI is not below the predetermined TTI value, a second algorithm is used to determine the first and second phase durations, wherein the first phase duration is not equal to the second phase duration.

2. The external defibrillator of claim 1, wherein the first algorithm or the second algorithm is based on a Walcott algorithm.

3. The external defibrillator of claim 1, wherein the first algorithm or the second algorithm is based on a constant energy (CE) algorithm.

4. The external defibrillator of claim 1, wherein the first algorithm or the second algorithm is based on a maximum duration algorithm.

5. The external defibrillator of claim 1, wherein first algorithm or the second algorithm is based on a modified Walcott algorithm.

6. The external defibrillator of claim 1, wherein the shock comprises a biphasic truncated exponential (BTE) waveform.

7. A method for an external defibrillator comprising two or more electrodes configured to be attached to a patient, an energy storage module, a discharge circuit coupled with the energy storage module and at least two of the two or more electrodes and configured to output energy from the energy storage module to the patient in a form of a shock, wherein the shock has a first phase duration and a second phase duration, an impedance measuring circuit to measure a transthoracic impedance (TTI) of the patient using at least some of the two or more electrodes, a memory to store a first shock algorithm and a second shock algorithm, and one or more processors coupled with the memory to control the impedance measuring circuit and the discharge circuit, the method comprising:
    measuring the TTI of the patient;
    causing the discharge circuit to apply the shock to the patient using the first shock algorithm when the TTI is below a predetermined TTI value, wherein the first phase duration is equal to the second phase duration; and
    causing the discharge circuit to apply the shock to the patient using the second shock algorithm when the TTI is below the predetermined TTI value, wherein the first phase duration is not equal to the second phase duration.

8. The method of claim 7, wherein the first shock algorithm or the second shock algorithm is based on a Walcott algorithm.

9. The method of claim 7, wherein first shock algorithm or the second shock algorithm is based on a modified Walcott algorithm.

10. The method of claim 7, wherein the first shock algorithm or the second shock algorithm is based on a constant energy (CE) algorithm.

11. The method of claim 7, wherein the first shock algorithm or the second shock algorithm is based on a maximum duration algorithm.

12. The method of claim 7, wherein the shock comprises a biphasic truncated exponential (BTE) waveform.

13. The method of claim 7, wherein the external defibrillator comprises a wearable cardioverter defibrillator (WCD).

14. A wearable cardioverter defibrillator (WCD), comprising:
    a support structure to be worn by a patient;
    two or more electrodes coupled with the support structure and configured to contact the patient when the patient is wearing the support structure;
    an energy storage module;
    a discharge circuit, coupled with the energy storage module and two or more defibrillation electrodes, wherein the discharge circuit is configured to output energy from the energy storage module;
an impedance measuring circuit; and
one or more processors, coupled with the impedance measuring circuit and the discharge circuit, wherein the one or more processors are configured to:
measure a transthoracic impedance (TTI) of the patient using the impedance measuring circuit; and
cause the discharge circuit to apply a shock having a first phase duration and a second phase duration to the patient using the two of the two or more electrodes, wherein:
when the TTI is below a predetermined TTI value, a first algorithm is used to determine the first and second phase durations, wherein the first phase duration is equal to the second phase duration; and
when the TTI is not below the predetermined TTI value, a second algorithm is used to determine the first and second phase durations, wherein the first phase duration is not equal to the second phase duration.

15. The WCD of claim 14, wherein the first algorithm or the second algorithm is based on a Walcott algorithm.

16. The WCD of claim 14, wherein first algorithm or the second algorithm is based on a modified Walcott algorithm.

17. The WCD of claim 14, wherein the first algorithm or the second algorithm is based on a constant energy (CE) algorithm.

18. The WCD of claim 14, wherein the first algorithm or the second algorithm is based on a maximum duration algorithm.

19. The WCD of claim 14, wherein the shock comprises a biphasic truncated exponential (BTE) waveform.

20. An external defibrillator, comprising:
two or more electrodes configured to contact a patient;
an energy storage module;
a discharge circuit, coupled to the energy storage module and at least two of the two or more electrodes;
an impedance measurement module configured to measure a transthoracic impedance (TTI) of the patient; and
one or more processors coupled to the discharge circuit and the impedance measurement module, the one or more processors configured to:
determine a shock duration, wherein responsive to a measured TTI being smaller than a threshold, the one or more processors are configured to determine the shock duration using a first algorithm, and responsive to the measured TTI not being smaller than the threshold, the one or more processors are configured to determine the shock duration using a second algorithm that is different from the first algorithm, and
cause the discharge circuit to output energy from the energy storage module to the patient in a form of a shock having the determined shock duration using at least two of the two or more electrodes.

* * * * *